(12) United States Patent
Lee et al.

(10) Patent No.: US 12,372,647 B2
(45) Date of Patent: Jul. 29, 2025

(54) SYSTEMS AND METHODS FOR PLANE WAVE COMPOUNDING IN ULTRASOUND IMAGING

(71) Applicant: Mayo Foundation for Medical Education and Research, Rochester, MN (US)

(72) Inventors: Hyungkyi Lee, Rochester, MN (US); Matthew W. Urban, Rochester, MN (US); James F. Greenleaf, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 18/561,254

(22) PCT Filed: Jul. 13, 2022

(86) PCT No.: PCT/US2022/036992
§ 371 (c)(1),
(2) Date: Nov. 15, 2023

(87) PCT Pub. No.: WO2023/287900
PCT Pub. Date: Jan. 19, 2023

(65) Prior Publication Data
US 2024/0248206 A1    Jul. 25, 2024

Related U.S. Application Data

(60) Provisional application No. 63/222,544, filed on Jul. 16, 2021.

(51) Int. Cl.
*G01S 15/89* (2006.01)
*A61B 8/00* (2006.01)

(52) U.S. Cl.
CPC .......... *G01S 15/8995* (2013.01); *A61B 8/485* (2013.01); *A61B 8/5207* (2013.01)

(58) Field of Classification Search
CPC .................. G01S 7/52042; G01S 15/8995
See application file for complete search history.

(56) References Cited

U.S. PATENT DOCUMENTS

| 11,885,877 | B2 * | 1/2024 | Samson | .............. G01S 15/8915 |
| 2020/0041644 | A1 * | 2/2020 | Brown | ................ G01S 15/8925 |

OTHER PUBLICATIONS

Lee, Hyoung-Ki, James F. Greenleaf, and Matthew W. Urban. "A new plane wave compounding scheme using phase compensation for motion detection." IEEE transactions on ultrasonics, ferroelectrics, and frequency control 69.2 (2021): 702-710.*

(Continued)

*Primary Examiner* — Carolyn A Pehlke
(74) *Attorney, Agent, or Firm* — Quarles & Brady LLP

(57) ABSTRACT

Systems and methods for Plane Wave Compounding ("PWC") are provided for improving image quality with reduced phase shift errors. The initial phase difference ("IPD") between two PW transmissions is related to the phase shift error. When the absolute value of IPD is larger than $\pi/2$, the phase shift error occurs. An Initial-Phase-Compensated PWC ("IPCPWC") method may be used to compensate the initial phase of echo signals from each PW transmit and maintain the absolute value of IPD smaller than $\pi/2$. IPCPWC methods may also include increased motion signal-to-noise ratio and reduced jitter.

20 Claims, 21 Drawing Sheets

(56) References Cited

OTHER PUBLICATIONS

Camacho, J. et al., Phase Coherence Imaging, IEEE Transactions on Ultrasonics, Ferroelectrics, and Frequency Control, 2009, 56(5):958-974.

Capriotti, M. et al., Time-Aligned Plane Wave Compounding Methods for High-Frame-Rate Shear Wave Elastography: Experimental Validation and Performance Assessment on Tissue Phantoms, Ultrasound in Medicine & Biology, 2021, 47(7): 1931-1948.

Chau, G. et al., Short-Lag Spatial Coherence Weighted Minimum Variance Beamformer for Plane-Wave Images, In 2016 IEEE International Ultrasonics Symposium (IUS), 2016, pp. 1-3.

Garcia, D. et al., Stolt's f-k Migration for Plane Wave Ultrasound Imaging, IEEE Transactions on Ultrasonics, Ferroelectrics, and Frequency Control, 2013, 60(9): 1853-1867.

Gong, P. et al., Delay-Encoded Harmonic Imaging (DE-HI) in Multiplane-Wave Compounding, IEEE Transactions on Medical Imaging, 2017, 36(4): 952-959.

Li, Y. et al., Angular Coherence in Ultrasound Imaging: Theory and Applications, Journal of the Acoustical Society of America, 2017, 141(3): 1582-1594.

Montaldo, G. et al., Coherent Plane-Wave Compounding for Very High Frame Rate Ultrasonography and Transient Elastography, IEEE Transactions on Ultrasonics, Ferroelectrics, and Frequency Control, 2009, 56(3):489-506.

Polichetti, M. et al., A Nonlinear Beamformer Based on p. th Root Compression-Application to Plane Wave Ultrasound Imaging, Applied Sciences, 2018, 8(4):599, pp. 1-15.

Song, P. et al., Coded Excitation Plane Wave Imaging for Shear Wave Motion Detection, IEEE Transactions on Ultrasonics, Ferroelectrics, and Frequency Control, 2015, 62(7): 1356-1372.

Synnevag, J. et al., Adaptive Beamforming Applied to Medical Ultrasound Imaging, IEEE Transactions on Ultrasonics, Ferroelectrics, and Frequency Control, 2007, 54(8): 1606-1613.

Tiran, E. et al., Multiplane Wave Imaging Increases Signal-to-Noise Ratio in Ultrafast Ultrasound Imaging, Physics in Medicine & Biology, 2015, 60:8549-8566.

Zhang, Y. et al., Ultrafast Ultrasound Imaging Using Combined Transmissions with Cross-Coherence-Based Reconstruction, IEEE Transactions on Medical Imaging, 2018, 37(2): 337-348.

Zhao, J. et al., Plane Wave Compounding Based on a Joint Transmitting-Receiving Adaptive Beamformer, IEEE Transactions on Ultrasonics, Ferroelectrics, and Frequency Control, 2015, 62(8): 1440-1452.

Zheng, C. et al., An Adaptive Imaging Method for Ultrasound Coherent Plane-Wave Compounding Based on the Subarray Zero-Cross Factor, Ultrasonics, 2020, 100:105978, pp. 1-10.

PCT International Search Report and Written Opinion, PCT/US2022/036992, Oct. 21, 2022, 15 pages.

* cited by examiner

SYSTEMS AND METHODS FOR PLANE WAVE COMPOUNDING IN ULTRASOUND IMAGING

STATEMENT REGARDING FEDERALLY SPONSORED RESEARCH

This invention was made with government support under R01HL145268 awarded by National Institutes of Health. The government has certain rights in the invention.

BACKGROUND

Since plane wave imaging ("PWI") was introduced two decades ago for tracking shear wave propagation, it has been utilized for many other applications including B-mode imaging, pulse wave imaging, Doppler imaging, microvascular imaging for functional ultrasound, and quantitative ultrasound. One of the primary benefits of PWI is the high frame rates which are limited by only the imaging depth. However, using unfocused plane wave transmissions leads to poorer image quality mainly due to a reduction in echo signal-to-noise (SNR).

One approach to improve the SNR using PWI is to use multiple angled plane wave transmissions. Then the received echoes are coherently summed, or compounded in a technique known as plane wave compounding ("PWC"). PWC can achieve image quality comparable to the multi-focal imaging method, but it requires more than 70 transmits at different angles. Moreover, PWC is known to suffer from the axial lobe and the side lobe artifacts with fewer transmissions for ultrafast acquisitions. Many adaptive beamforming techniques have been proposed to preserve both resolution and contrast of B-mode images while maintaining high frame rates. These methods place emphasis on the improvement of B-mode image quality and did not investigate the metrics related to motion estimation.

Regarding phase shift estimation that can be used for measuring tissue motion, some of the advanced beamforming methods such as a frequency domain technique, minimum variance, phase coherence factor, and nonlinear delay-and-sum were experimentally compared with the conventional delay-and-sum algorithm. Their results suggest that a strong adaptive effect for resolution and contrast improvements of B-mode imaging can degrade the performance of the particle velocity estimation.

In many applications of ultrafast imaging, the particle velocity is of concern rather than the B-mode image quality. In shear wave elastography, PWC with a smaller number of angles suffers from the limited penetration depth of the plane waves and the poor SNR of shear wave motion. Coded excitation plane wave imaging was proposed to address these challenges. Both phase encoding (Barker code) and frequency encoding (chirp code) methods were investigated and showed significantly higher sensitivity to shear wave motion and robustness to weak ultrasound signals. Multi-plane wave ("MW") compounding was proposed to increase the image SNR without sacrificing the resolution or frame rate. In MW imaging, multiple plane waves are emitted quasi-simultaneously with differently coded amplitudes and emission angles. The received data of successive events are decoded through addition or subtraction to obtain signals from single angle PW with increased amplitude. Harmonic imaging was combined with MW imaging and delay-encoded harmonic imaging was proposed to reduce the reverberation artifacts due to longer transmitted pulses of MW.

Previously, PWC motion was calculated between two consecutive compounded images using one-dimensional ("1D") cross-correlation. Motion was also estimated by using two speckle images corresponding to plane wave insonifications with the same angles. Both methods result in the reduction of the frame rate of the motion images compared to that of the speckle images because of a tradeoff between the number of plane wave angles and acquisition time. To preserve the frame rate for a Doppler estimation, a sliding window approach utilized the moving average along the frame axis. Time-Aligned Plane Wave Compounding ("TA PWC") was introduced to maintain a high pulse repetition frequency. This method utilized interpolation to obtain data points at higher frame rates, and the time-aligned data was compounded to increase the SNR.

Plane wave transmission has enabled a number of new applications such as shear wave elastography, ultrafast Doppler imaging, and functional ultrasound imaging. PWC, which as noted above coherently sums the echo signals from multiple plane wave transmits with different angles, is widely used to improve B-mode image quality. When the motion between two speckle images is estimated, however, PWC inherently suffers from a phase shift error.

What are needed are methods for PWC to improve ultrasound image quality that do not suffer from phase shift errors.

SUMMARY OF THE DISCLOSURE

The present disclosure addresses the aforementioned drawbacks by providing systems and methods for ultrasound Plane Wave Compounding ("PWC") with improved image quality with reduced phase shift errors. The initial phase difference ("IPD") between two PW transmissions is related to the phase shift error. When the absolute value of IPD is larger than $\pi/2$, the phase shift error occurs. An Initial-Phase-Compensated PWC ("IPCPWC") method in accordance with the present disclosure compensates the initial phase of echo signals from each PW transmission and maintains the absolute value of IPD smaller than $\pi/2$.

In one configuration, a method is provided for ultrasound plane wave compounding imaging. The method includes accessing ultrasound plane wave time series data with a computer system. The ultrasound plane wave time series data may have been acquired from a region of a subject and includes ultrasound plane wave data acquired for a plurality of different transmission angles at each of a plurality of time points. The method also includes selecting a first data set from the ultrasound plane wave time series data corresponding to ultrasound plane wave data acquired for the plurality of the different transmission angles at a first time point. The method also includes selecting a second data set from the ultrasound plane wave time series data corresponding to ultrasound plane wave data acquired for the plurality of the different transmission angles at a second time point that is subsequent to the first time point. The method also includes calculating with the computer system for each of the plurality of different transmission angles, an initial phase angle mean value between ultrasound plane wave data in the first data set and the second data set corresponding to a common one of the plurality of the different transmission angles. The method also includes generating initial-phase-compensated plane wave data by adjusting the ultrasound plane wave data in the first data set and the second data set using the initial phase angle mean values calculated for each of the plurality of different transmission angles. The method also includes constructing phase-compensated images from the initialphase-compensated plane wave data. The phase-compensated images depict the region of the subject at the first time point and the second time point.

In one configuration, a system is provided for ultrasound plane wave compounding imaging. The system includes an ultrasound imaging system configured for plane wave compounding imaging. The system also includes a computer system configured to: access ultrasound plane wave time series data. The ultrasound plane wave time series data may have been acquired from a region of a subject and includes ultrasound plane wave data acquired for a plurality of different transmission angles at each of a plurality of time points. The computer system is also configured to select a first data set from the ultrasound plane wave time series data corresponding to ultrasound plane wave data acquired for the plurality of the different transmission angles at a first time point. The computer system is also configured to select a second data set from the ultrasound plane wave time series data corresponding to ultrasound plane wave data acquired for the plurality of the different transmission angles at a second time point that is subsequent to the first time point. The computer system is also configured to calculate with the computer system for each of the plurality of different transmission angles, an initial phase angle mean value between ultrasound plane wave data in the first data set and the second data set corresponding to a common one of the plurality of the different transmission angles. The computer system is also configured to generate initial-phase-compensated plane wave data by adjusting the ultrasound plane wave data in the first data set and the second data set using the initial phase angle mean values calculated for each of the plurality of different transmission angles. The computer system is also configured to construct phase-compensated images from the initial-phase-compensated plane wave data. The phase-compensated images depict the region of the subject at the first time point and the second time point.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention. Like reference numerals will be used to refer to like parts from Figure to Figure in the following description.

DETAILED DESCRIPTION

Systems and methods for Plane Wave Compounding ("PWC") are provided for improving image quality with reduced phase shift errors. The initial phase difference ("IPD") between two PW transmissions is related to the phase shift error. When the absolute value of IPD is larger than $\pi/2$, the phase shift error occurs. An Initial-Phase-Compensated PWC ("IPCPWC") method in accordance with the present disclosure compensates the initial phase of echo signals from each PW transmission and maintains the absolute value of IPD smaller than $\pi/2$. In a non-limiting example, the increased signal-to-noise ratio and reduced jitter of IPCPWC are demonstrated using tissue mimicking phantoms compared to PWC.

Systems and methods in accordance with the present disclosure may provide for increasing the SNR of motion between two compounded images. Motion error in PWC may be derived theoretically and may be demonstrated experimentally. This error is related to the magnitude of the initial phase difference between plane wave transmissions with different angles. To address or mitigate this artifact, IPCPWC may be used in accordance with the present disclosure.

Figure 1:
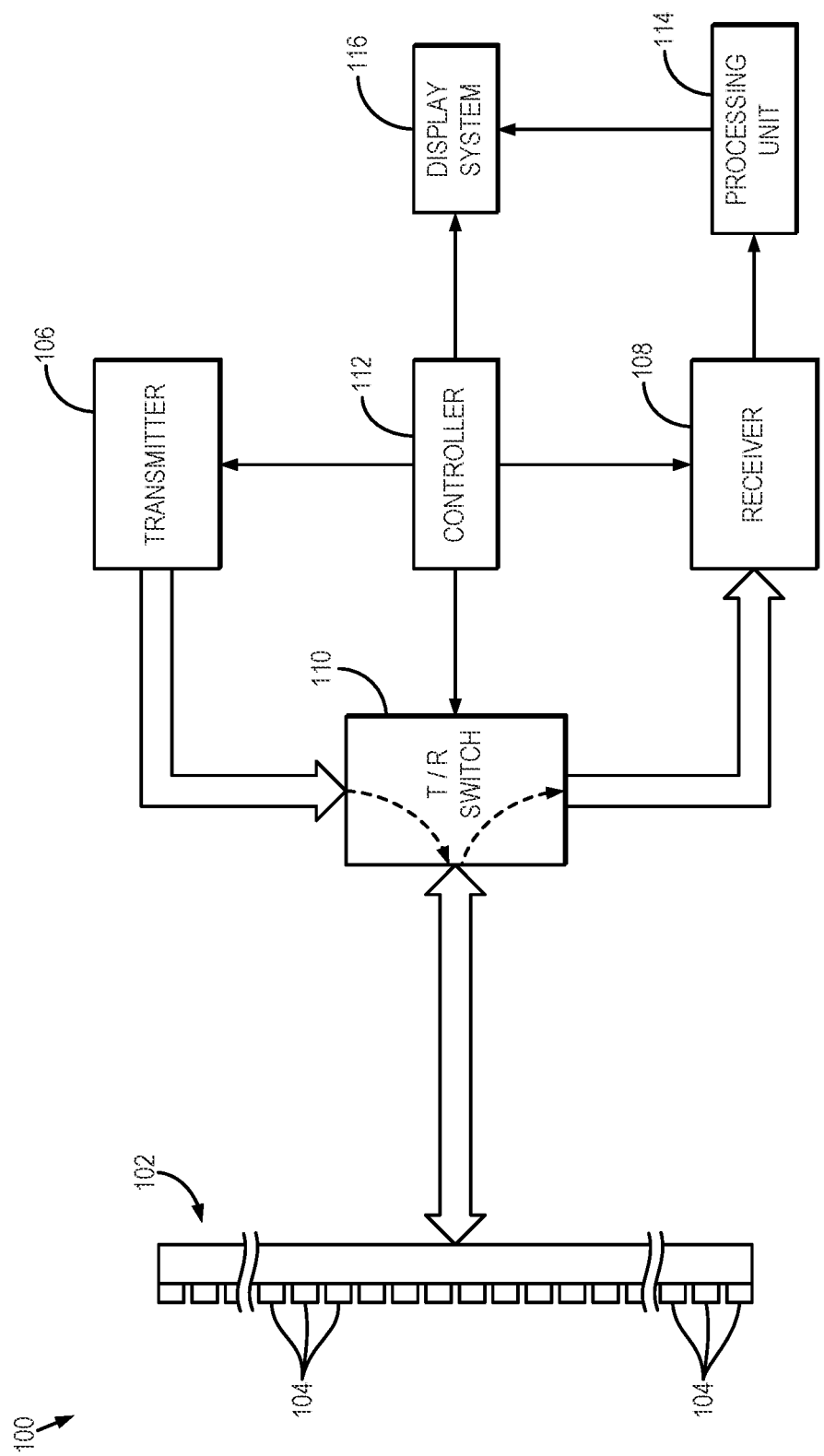
FIG. 1 is a block diagram of a non-limiting example ultrasound system that may implement the systems and methods of the present disclosure.

FIG. 1 illustrates an example of an ultrasound system 100 that can implement the methods described in the present disclosure. The ultrasound system 100 includes a transducer array 102 that includes a plurality of separately driven transducer elements 104. The transducer array 102 can include any suitable ultrasound transducer array, including linear arrays, curved arrays, phased arrays, and so on. Similarly, the transducer array 102 can include a 1D transducer, a 1.5D transducer, a 1.75D transducer, a 2D transducer, a 3D transducer, and so on.

When energized by a transmitter 106, a given transducer element 104 produces a burst of ultrasonic energy. The ultrasonic energy reflected back to the transducer array 102 (e.g., an echo) from the object or subject under study is converted to an electrical signal (e.g., an echo signal) by each transducer element 104 and can be applied separately to a receiver 108 through a set of switches 110. The transmitter 106, receiver 108, and switches 110 are operated under the control of a controller 112, which may include one or more processors. As one example, the controller 112 can include a computer system.

The transmitter 106 can be programmed to transmit unfocused or focused ultrasound waves. In some configurations, the transmitter 106 can also be programmed to transmit diverged waves, spherical waves, cylindrical waves, plane waves, or combinations thereof. Furthermore, the transmitter 106 can be programmed to transmit spatially or temporally encoded pulses.

The receiver 108 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 106 and the receiver 108 can be programmed to implement a high frame rate. For instance, a frame rate associated with an acquisition pulse repetition frequency ("PRF") of at least 100 Hz can be implemented. In some configurations, the ultrasound system 100 can sample and store at least one hundred ensembles of echo signals in the temporal direction.

The controller 112 can be programmed to design an imaging sequence using the techniques described in the present disclosure, or as otherwise known in the art. In some embodiments, the controller 112 receives user inputs defining various factors used in the design of the imaging sequence.

A scan can be performed by setting the switches 110 to their transmit position, thereby directing the transmitter 106 to be turned on momentarily to energize transducer elements 104 during a single transmission event according to the designed imaging sequence. The switches 110 can then be set to their receive position and the subsequent echo signals produced by the transducer elements 104 in response to one or more detected echoes are measured and applied to the receiver 108. The separate echo signals from the transducer elements 104 can be combined in the receiver 108 to produce a single echo signal.

The echo signals are communicated to a processing unit 114, which may be implemented by a hardware processor and memory, to process echo signals or images generated from echo signals. As an example, the processing unit 114 can implement a plane wave compounding scheme to reduce the error in phase shift estimation for shear wave motion detection using the methods described in the present disclosure. Images produced from the echo signals by the processing unit 114 can be displayed on a display system 116.

In the PWC method, by applying different time-delays to the array elements, multiple plane waves are consecutively emitted to the same imaging region at different angles. The final PWC image is obtained by coherently combining the images acquired from several emitting plane waves. Two consecutive PWC images, R and S at times of $T_i$ and $T_{i+1}$ are obtained by $$R = \frac{1}{N}\sum_{n=1}^{N} r_n(x, z, T_i) \quad (1)$$

$$S = \frac{1}{N}\sum_{n=1}^{N} s_n(x, z, T_{i+1})$$

where $r_n$ and $s_n$ are the received in-phase/quadrature ("IQ") signals of the plane waves transmitted with the nth inclination angle, N is the total angles of plane wave transmits, and x and z are the lateral and axial positions. In some alternative implementations, the received signals, $r_n$ and $s_n$, can be radio frequency ("RF") signals of the plane waves. Rather than IQ signals, as described below in more detail. When the signals are IQ signals, in general, $r_1 \ldots r_N$ are assumed to be at the same time of $T_i$ ignoring the time lapse between $r_1$ and $r_N$.

When $s_n$ is a time delayed signal from $r_n$ by $\delta t$, $s_n$ and $r_n$ are represented by $$r_n = A_n(t) \cdot e^{i\varphi_n}, \quad (2)$$

$$s_n = A_n(t) \cdot e^{i(\omega_c \delta t + \varphi_n)}$$

where t is the time along the depth dimension, $A_n$ is the amplitude of the signal, $\omega_c$ is the center frequency of the carrier signal, and $\varphi_n$ is the initial phase angle of the nth transmit angle. Here, it can be assumed that the magnitude of the IQ signal does not change during the interval of two plane wave transmits; thus, $r_n$ and $s_n$ have the same amplitude.

The phase shift between two consecutive compounded images can be obtained by $$\delta\theta = ang(S \times R^*) = ang\left(\frac{1}{N^2}\left(\sum_{n=1}^{N} s_n \cdot r_n^* + \sum_{n \neq m} s_n \cdot r_m^*\right)\right) \quad (3)$$

where * denotes the complex conjugate and ang ( ) represents the phase of a complex number.

Figures 2, 3:
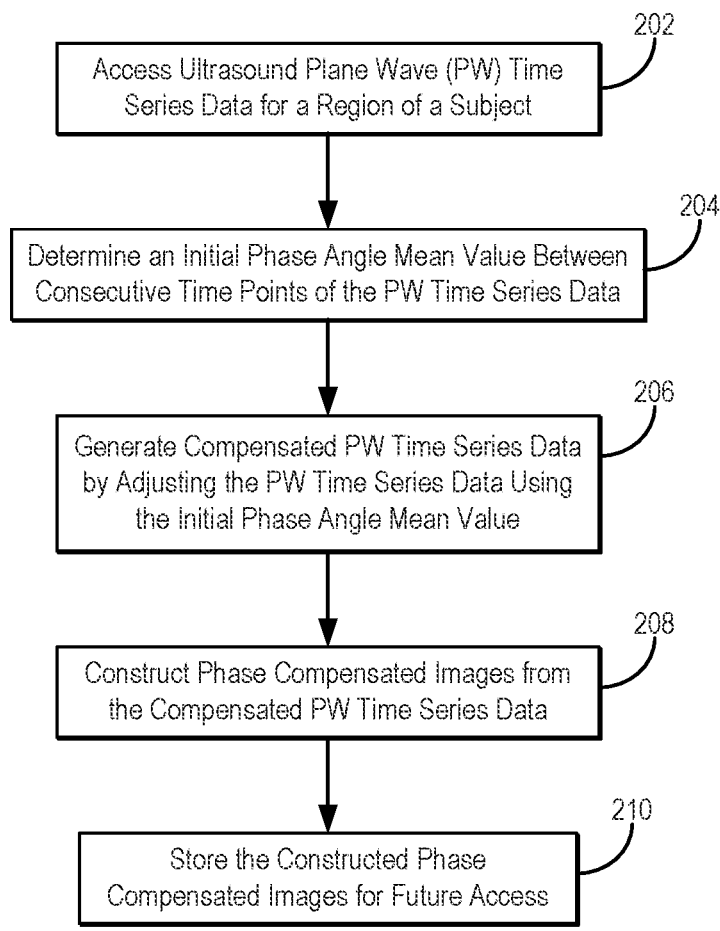
FIG. 2 is a flow chart of non-limiting example steps for a plane wave compounding scheme to reduce the error in phase shift estimation for shear wave motion detection.
FIG. 3 a non-limiting example matrix is shown for a phase shift estimation using PWC in a matrix form.

Referring to FIG. 3, a non-limiting example matrix is shown for a phase shift estimation using PWC in a matrix form. The diagonal terms calculate the phase shift between two consecutive signals from plane waves transmitted with the same angle and the off-diagonal terms deal with the signals from plane waves transmitted with the different angles. The left and right summation of Eq. (3) can be considered as the sums of the diagonal terms and the off-diagonal terms of the matrix respectively. Off-diagonal terms tend to contribute more motion noise than the diagonal terms. The phase shift from the diagonal and off-diagonal terms may be examined separately.

The phase shift from the diagonal terms is given by $$s_n \cdot r_n^* = A_n e^{i(\omega_c \delta t + \varphi_n)} \times A_n e^{-i\varphi_n} = A_n A_n e^{i\omega_c \delta t}. \quad (4)$$

This yields $$ang(s_n \cdot r_n^*) = \omega_c \delta t. \quad (5)$$

From this equation, the time delay $\delta t$ can be calculated with a known $\omega_c$. Note that the initial phase on is cancelled and does not remain in Eq. (5).

The right summation of Eq. (3) involves two signals from the different angle transmits. The term $s_n \cdot r^*_m$ is given by $$s_n \cdot r^*_m = A_n e^{i(\omega_c \delta t + \varphi_n)} \times A_m e^{-i\varphi_m} \qquad (6)$$
$$= A_n A_m e^{i(\omega_c \delta t + \Delta\varphi_{nm})}$$

where $\Delta\varphi_{nm} = \Phi_n - \varphi_m$. We will refer to $\Delta\varphi_{nm}$ as initial phase difference or IPD hereafter. Because the IPD is added to $\omega_c \delta t$ in the phase of Eq. (6), the correct phase shift of $\omega_c \delta t$ cannot be directly obtained from Eq. (6). When $s_m \cdot r^*_n$ is added to Eq. (6), the upper right and lower left off-diagonal terms of the matrix of FIG. 3 may be calculated together. In some configurations, it is worth examining if the IPD can be cancelled.

$$s_n \cdot r^*_m + s_m \cdot r^*_n = \qquad (7)$$
$$A_n A_m \cdot e^{i\omega_c \delta t}\left(e^{i\Delta\varphi_{nm}} + e^{-i\Delta\varphi_{nm}}\right) = 2A_n A_m \cdot e^{i\omega_c \delta t} \cdot \cos(\Delta\varphi_{nm}) =$$
$$\begin{cases} 2\cos(\Delta\varphi_{nm}) \cdot A_n A_m \cdot e^{i\omega_c \delta t}, \text{ for } \cos(\Delta\varphi_{nm}) \geq 0 \\ 2|\cos(\Delta\varphi_{nm})| \cdot A_n A_m \cdot e^{i(\omega_c \delta t + \pi)}, \text{ for } \cos(\Delta\varphi_{nm}) < 0 \end{cases}$$

when $\cos(\Delta\varphi_{nm}) \geq 0$ is satisfied, the phase of this off-diagonal pair is the phase shift of $\omega_c \delta t$. To satisfy this, the absolute value of the IPD of $\Delta\varphi_{nm}$ should be less than $\pi/2$. This condition is not guaranteed for all pixels. Some pixels meet this condition and other pixels do not. Assuming $\cos(\Delta\varphi_{nm}) \geq 0$, substituting Eq. (7) and Eq. (4) into Eq. (3) yields $$\delta\theta = ang(S \times R^*) = \qquad (8)$$
$$ang\left(\frac{1}{N^2}\left(\sum_{n=1}^N A_n A_n + \sum_{m>n} 2\cos(\Delta\varphi_{nm}) \cdot A_n A_m\right) e^{i\omega_c \delta t}\right) = \omega_c \delta t$$

The phase shift of PWC gives the exact phase shift.

In the case of $\cos(\Delta\varphi_{nm}) < 0$, the added error of $\pi$ appears in the phase of Eq. (7) and gives an inaccurate phase shift estimation. This suggests that IPD of $\Delta\varphi_{nm}$ is a factor to the error caused by the off-diagonal terms. To calculate the IPD of $\Delta\varphi_{nm}$, the following equation can be used from Eq. (6):

$$\Delta\varphi_{nm} = (ang(s_n \cdot r^*_m) - ang(s_m \cdot r^*_n))/2. \qquad (9)$$

Thus, in some instances, the calculation of the phase shift between two compounded images of $R(t=t_i)=r_1+r_2+\ldots r_N$ and $S(t=t_{i+1})=s_1+s_2+\ldots s_N$, will include errors introduced by motion calculations between $r_n$ and $s_m$ ($n \neq m$) (i.e., between different angle transmissions) than between $r_n$ and $s_n$ (i.e., the same angle transmissions). This error is related to the initial phase difference (IPD) between plane wave transmissions with nth and mth angles, which can be defined as $ang(r_n) - ang(r_m)$ where $ang()$ represents the phase of a complex number. When the absolute value of IPD is larger than $\pi/2$, the phase shift error occurs. IPCPWC compensates the initial phase of echo signals from each PW transmit and maintains the absolute value of IPD smaller than $\pi/2$.

For preventing the inaccurate phase shift estimation between the off-diagonal pair of PWC, a method to compensate the initial phase of $r_n$ and $s_n$ may be used.

The compensated IQ signals may be defined by $$\bar{r}_n = A_n e^{i(\varphi_n - \bar{\varphi}_n)} \qquad (10)$$
$$\bar{s}_n = A_n e^{i(\omega_c \delta t + \varphi_n - \bar{\varphi}_n)}$$

where $\bar{\varphi}_n$ is the mean value of the angle of r and s, that is $$\bar{\varphi}_n = \frac{ang(r_n) + ang(s_n)}{2}.$$

$\varphi_n - \bar{\varphi}_n$ can be calculated by $$\varphi_n - \bar{\varphi}_n = -\frac{\omega_c \delta t}{2}. \qquad (11)$$

Compounded images $\bar{R}$ and $\bar{S}$ may be constructed as follows:

$$\bar{R} = \frac{1}{N}\sum_{n=1}^N \bar{r}_n \qquad (12)$$

$$\bar{S} = \frac{1}{N}\sum_{n=1}^N \bar{s}_n.$$

Using these equations, the phase shift, $\delta\theta$ can be obtained by $$\delta\theta = ang(\bar{S} \times \bar{R}^*) = ang\left(\frac{1}{N^2}\left(\sum_{n=1}^N \bar{s}_n \cdot \bar{r}^*_n + \sum_{n \neq m} \bar{s}_n \cdot \bar{r}^*_m\right)\right). \qquad (13)$$

The left summation of Eq. (13) is given by $$\bar{s}_n \cdot \bar{r}^*_n = A_n e^{i(\omega_c \delta t + \varphi_n - \bar{\varphi}_n)} \times A_n e^{-i(\varphi_n - \bar{\varphi}_n)} \qquad (14)$$
$$= A_n A_n e^{i\omega_c \delta t}.$$

The angle of $\bar{s}_n \cdot \bar{r}^*_n$ becomes $\omega_c \delta t$ and the term $\varphi_n - \bar{\varphi}_n$ is cancelled. The right summation of Eq. (13) is given by $$\bar{s}_n \cdot \bar{r}^*_m = A_n e^{i(\omega_c \delta t + \varphi_n - \bar{\varphi}_n)} \times A_m e^{-i(\varphi_m - \bar{\varphi}_m)} \qquad (15)$$
$$= A_n A_m e^{i(\omega_c \delta t + \varphi_n - \bar{\varphi}_n - \varphi_m + \bar{\varphi}_m)}.$$

A pair of the off-diagonal terms is calculated as follows:

$$\bar{s}_n \cdot \bar{r}^*_m + \bar{s}_m \cdot \bar{r}^*_n = A_n A_m e^{i\omega_c \delta t}\left(e^{i(\varphi_n - \bar{\varphi}_n - \varphi_m + \bar{\varphi}_m)} + e^{-i(\varphi_n - \bar{\varphi}_n - \varphi_m + \bar{\varphi}_m)}\right) \qquad (16)$$
$$= A_n A_m e^{i\omega_c \delta t} \cdot 2\cos(\varphi_n - \bar{\varphi}_n - \varphi_m + \bar{\varphi}_m).$$

From Eq. (11), $\varphi_n - \bar{\varphi}_n - \varphi_m + \bar{\varphi}_m$ becomes zero and it yields $\cos(\varphi_n - \bar{\varphi}_n - \varphi_m + \bar{\varphi}_m) = 1$. Therefore, the following can be obtained from Eq. (16).

$$\overline{s}_n \cdot \overline{r}_m^* + \overline{s}_m \cdot \overline{r}_n^* = 2A_n A_m e^{i\omega_c \delta t}. \quad (17)$$

Substituting Eq. (17) and (14) into Eq. (13) leads to $$\delta\theta = ang(\overline{S} \times \overline{R}^*) \quad (18)$$
$$= ang\left(\frac{1}{N^2}\left(\sum_{n=1}^{N} A_n A_n + \sum_{m>n} 2A_n A_m\right)e^{i\omega_c \delta t}\right)$$
$$= \omega_c \delta t.$$

The time delay δt can be correctly obtained from ang($\overline{S} \times \overline{R}^*$) with the known $\omega_c$.

When $r_n$ and $s_n$ are RF signals instead of IQ signals, they can be modeled in a complex form by:
they can be modeled in a complex form by $$r_n = A_n(t) \cdot e^{i(\omega_c t + \varphi_n)}, \quad (19)$$
$$s_n = A_n(t) \cdot e^{i(\omega_c(t+\delta t) + \varphi_n)}$$

Using $$\overline{\varphi}_n = \frac{ang(r_n) + ang(s_n)}{2},$$

$\overline{\varphi}_n$ can be calculated by $$\overline{\varphi}_n = \omega_c t + \varphi_n + \frac{\omega_c \delta t}{2} \quad (20)$$

The compensated RF signals are expressed by $$\overline{r}_n = A_n e^{i(\omega_c t + \varphi_n - \overline{\varphi}_n)} \quad (21)$$
$$\overline{s}_n = A_n e^{i(\omega_c(t+\delta t) + \varphi_n - \overline{\varphi}_n)}$$

Repeating the same calculation as in the case of IQ signals, the phase shift can be obtained by:

$$\delta\theta = ang(\overline{S} \times \overline{R}^*) = \omega_c \delta t. \quad (22)$$

Referring to FIG. 2, a flow chart of non-limiting example steps for a method of IPCPWC is shown. Ultrasound plane wave time series data for a region of a subject may be accessed at step 202. Accessing the plane wave time series data can include retrieving previously acquired plane wave time series data from a memory or other data storage device or medium. Additionally or alternatively, accessing the plane wave time series data can include acquiring the data with a suitable ultrasound system and communicating or otherwise transferring the data to the computer system, which in some instances may be a part of the ultrasound system. In general, the plane wave time series data include ultrasound data acquired for a plurality of different transmission angles over a period of time.

An initial phase angle mean value between data acquired at subsequent or consecutive time points of the plane wave time series data may be determined at step 204. A second time point can be any time after a first time point. In a non-limiting example, the second time point is consecutive to the first time point. The data at two different time points are compared to apply the methods in accordance with the present disclosure. For instance, first data, $r_n$, can be data acquired at a first time point for a transmission angle n, and second data, $s_n$, can be data acquired at a second subsequent or consecutive time point for a transmission angle n. The subsequent or consecutive time points may be separated by a time delay. In some implementations, computing the initial phase angle mean values can include selecting a first data set corresponding to these first data, $r_n$, acquired at the first time point and a second data set corresponding to these second data, $s_n$, acquired at a second, consecutive time point. The initial phase angle mean values, $\overline{\varphi}n$, are then computed for each transmission angle, n, using the selected first and second data sets. As a non-limiting example, the initial phase angle mean values can be computed according to $$\overline{\varphi}_n = \frac{ang(r_n) + ang(s_n)}{2}.$$

Compensated plane wave time series data may be generated by adjusting the first and second data selected from the plane wave time series data acquired for the nth transmission angle using the initial phase angle mean value calculated between the first and second data acquired with that transmission angle, n, as indicated at step 206. In some configurations, generating compensated plane wave time series data includes subtracting the initial phase angle mean value from the phase value of the first and second data acquired with the corresponding transmission angle, as described above. For instance, these initial-phase-compensated ultrasound plane wave data can be computed according to Eq. (10) above.

Phase compensated images may be constructed from the compensated plane wave time series data at step 208. In some configurations, the constructed images are compounded images as a sum of the time series data over a plurality of angles. For instance, phase-compensated images can be constructed according to Eqn. (12) above.

The constructed phase compensated images may be stored for future use or accessed at step 210, such as for shear wave elastography, ultrafast Doppler imaging, functional ultrasound imaging, improving ultrasound B-mode image quality, and the like.

As a non-limiting example, phase shifts can be estimated from the phase-compensated images and used to estimate shear wave motion when one or more shear waves are induced in the region of the subject prior to data acquisition. The phase shift can be calculated according to Eq. (18) above and the resulting motion data can be used in shear wave elastography techniques to compute or otherwise estimate mechanical or other material properties of the subject, including viscoelastic properties.

Phantom studies were performed using elasticity quality assurance phantoms (Model 039) with four different stiffness of Young's modulus E=3.5, 10, 25 and 45 kPa and a multi-purpose quality assurance phantom (Model040 GSE) manufactured by CIRS, Inc. (Norfolk, VA, USA). A Verasonics ultrasound system (V1, Verasonics Inc., Kirkland, WA, USA) was used to produce the ultrasound push beam using acoustic radiation force ("ARF") and track the shear wave propagation using ultrafast plane wave imaging. The PW tracking excited all transducer elements with the time delays to steer the beam and the angular compounding using three angles [−10°, 0°, 10°] was adopted. The L7-4 linear array probe (Philips Healthcare, Andover, MA) with a center frequency of 5 MHz was used. One focused push beam (center frequency=4.1 MHz, F #=2, focal depth=40 mm, push line at x=10.3 mm) was transmitted with a duration of 400 μsec. The shear wave tracking had a center frequency of 5 MHz and its frame rate was 10 KHz. The Verasonics system provides the beamformed IQ data. The transmit voltage was set at ±50 V, and it applied to both the push transmission and plane wave transmission.

The motion data were obtained using two methods of PWC and IPCPWC. The compounded image for PWC was constructed using Eq. (1). Equation (10) was utilized for IPCPWC and the mean value of the initial phase ($\bar{\varphi}_n$) was calculated after applying a phase unwrapping function (unwrap.m) in MATLAB (Mathworks, Inc., Natick, MA, USA) to the phase of the IQ data. This may be used to avoid the discontinuity of the phase when the phase crosses from $+\pi$ to $-\pi$ and vice versa. We calculated the time delay between the IQ data of two consecutive compounded images, which corresponds to the particle velocity profile (i.e., time derivative of the displacement profile). A ID autocorrelation method (Kasai method) was used as a time delay estimation algorithm with the kernel size of 1.5λ. No filtering was applied to the motion data. The final motion data were 322×256 spatial pixels (with axial and lateral spatial resolution of 0.154 mm and 0.149 mm) and 150 frames in time.

Shear wave SNR and jitter were used as metrics to quantify the performance of the methods. Jitter was measured as the standard deviation ("SD") of the motion errors. To obtain the ground truth ("GT") of the motion (or shear wave signal for SNR), 10 measurements were repeated and averaged. Before the averaging, a 2D median filter with window size of 3×3 can be applied to the motion data. The SNR was calculated by the ratio of the RMS (root mean square) value of the shear wave signal to the RMS of the motion error.

Referring to FIGS. 4A-4D, graphs of non-limiting example initial phase difference data are shown. To examine the motion error caused by the IPD in PWC, some examples of the IPD were acquired using commercial CIRS phantoms. The IPD was calculated utilizing Eq. (9). Because plane waves with the three angles of [−10°,0°, 10°] were used in the experiments, three IPDs of $\Delta\varphi_{0,-10}$, $\Delta\varphi_{10,-10}$, and $\Delta\varphi_{10,0}$ can be obtained. The IPD of $\Delta\varphi_{0,-10}$ is plotted in FIG. 4D as a representative case and the other IPDs show similar results. The IPD varies across the pixels in the xz-plane as shown. The values range from $-\pi$ to $\pi$ and do not show any specific pattern. At z=40 mm, IPD over time was plotted as shown. To see the changes of the IPD over time more clearly, the AC component is also displayed. At each lateral position, the mean value of IPD over time was computed and this was subtracted from the original signal. Most of the IPDs change slightly but at some positions the IPDs show a lot of variance over time. The correlation between IPD and the magnitude of the IQ signal is shown at each location. The complete IQ signal set was three-dimensional ("3D") array data including the echo signal through time throughout a two-dimensional ("2D") field-of-view and they were all processed to obtain the correlation plot. The magnitude of the IQ signal is the product of the magnitude of two IQ signals, which are received from plane wave transmissions with 0° and −10°. The lines represent $-\pi/2$ and $\pi/2$. The points with the higher magnitude tend to have the smaller IPD values. The absolute values of IPD are greater than $\pi/2$ at many points (i.e. $\cos(\Delta\varphi_{nm})<0$) and these points cause the error of the phase shift estimation.

Figure 5:
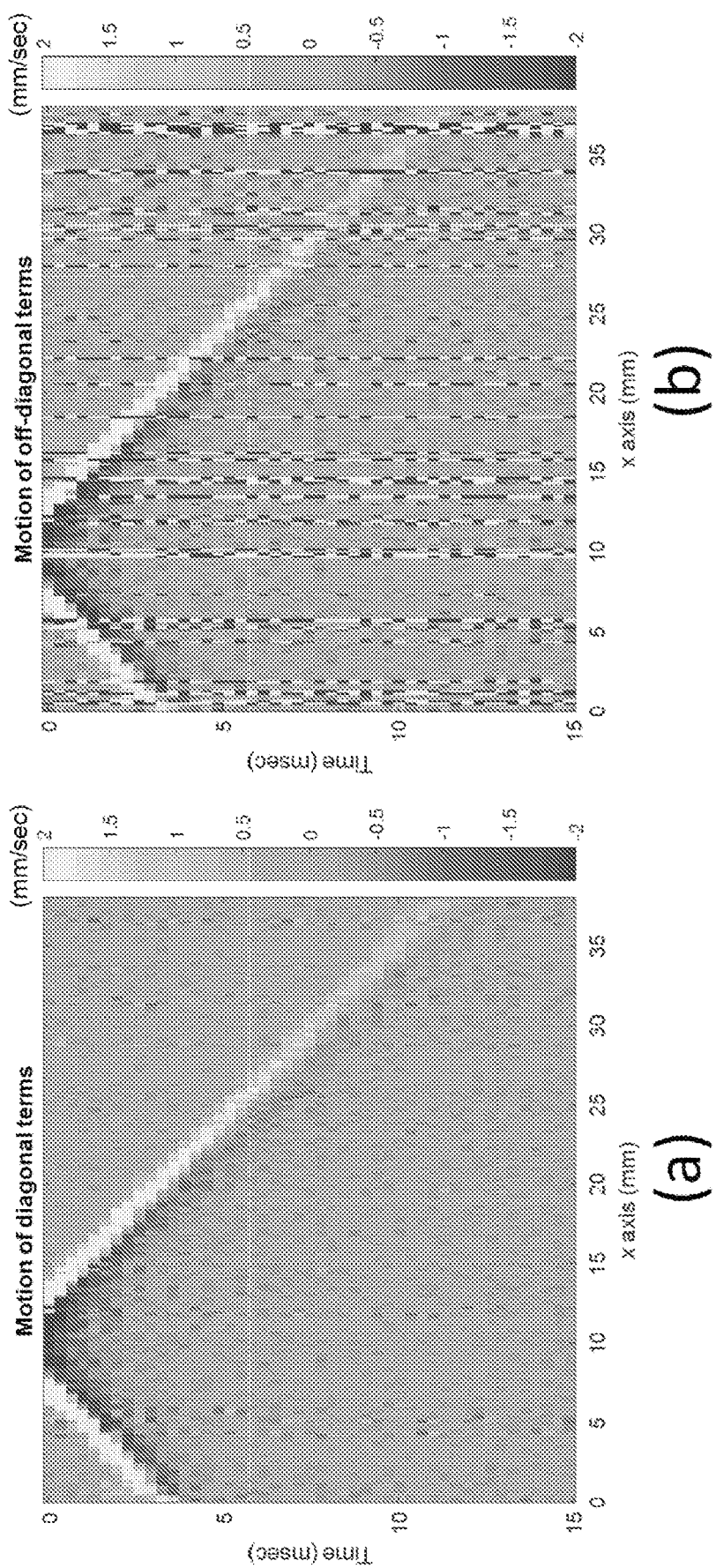
FIG. 5 are non-limiting example graphs of a comparison between the motion from the diagonal terms to that from the off-diagonal terms.
Figures 6A, 6B:
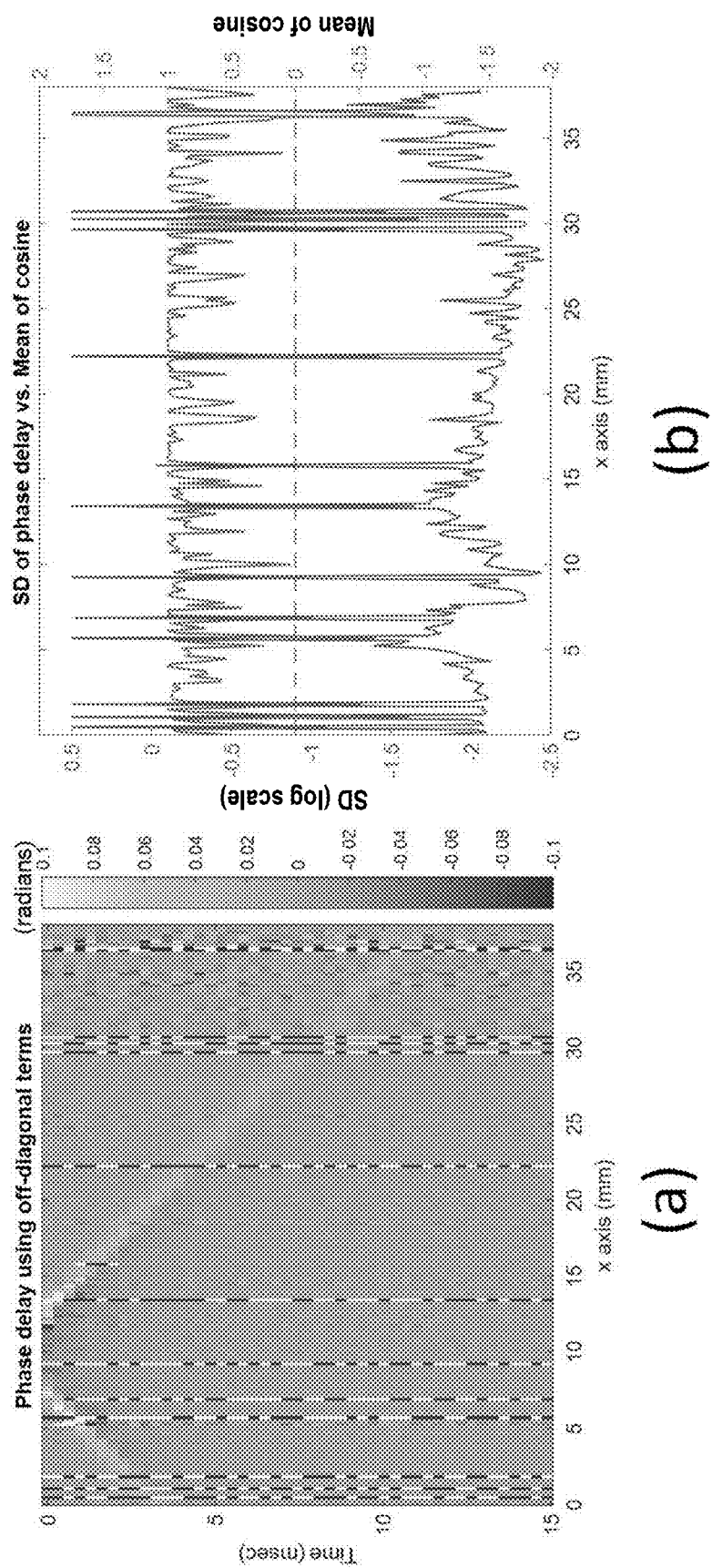
FIGS. 6A-6D are graphs of a non-limiting example comparison between phase shifts from the off-diagonal terms between PWC and IPCPWC.
Figures 6C, 6D:
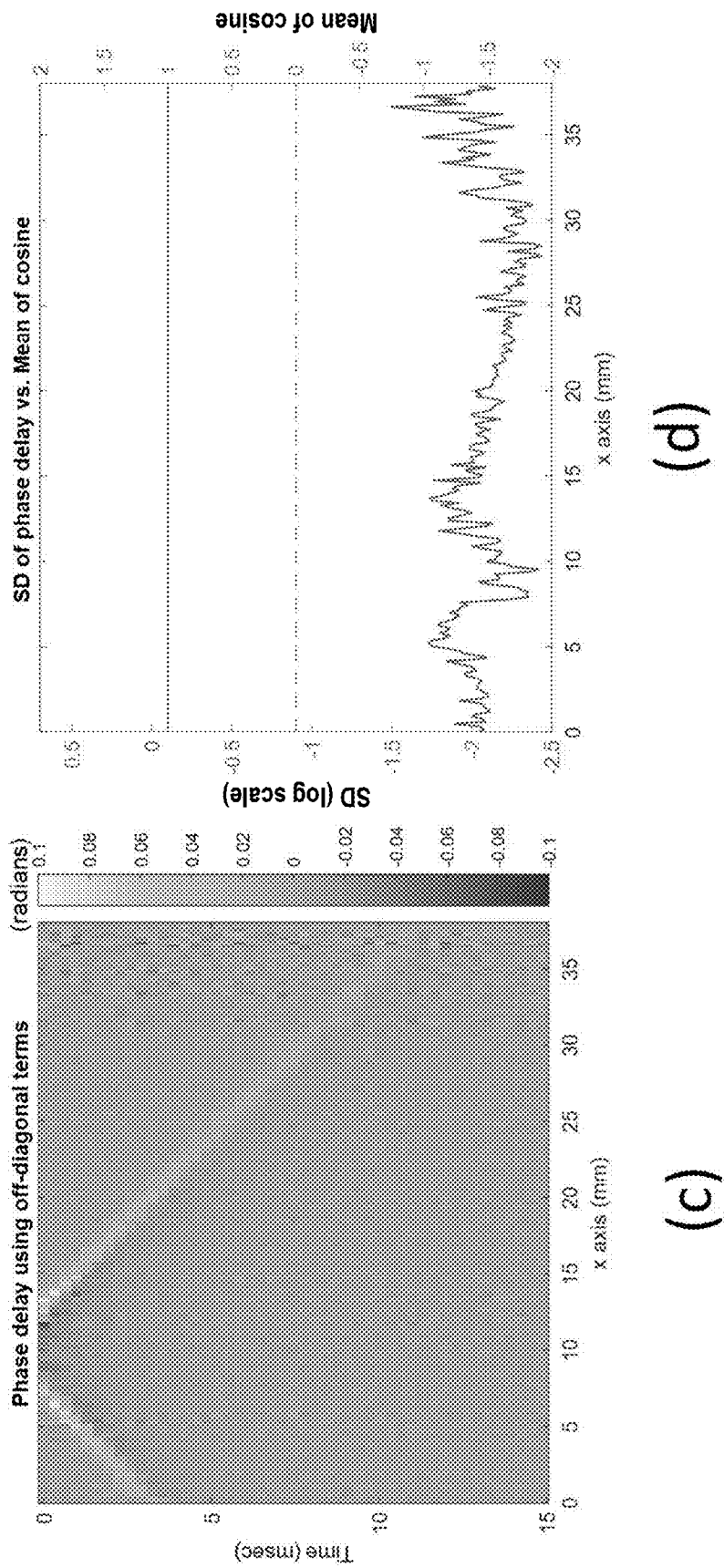

Referring to FIG. 5, non-limiting example graphs are shown of a comparison between the motion from the diagonal terms to that from the off-diagonal terms. The motion at z=40 mm is shown after calculating the left summation of Eq. (3), and the right summation of Eq. (3). As can be seen, the off-diagonal terms have more errors than the diagonal terms.

Referring to FIGS. 6A-6D, a non-limiting example comparison between phase shifts from the off-diagonal terms between PWC and IPCPWC is shown. The motion from the off-diagonal terms gives incorrect estimations in the conventional PWC when the absolute value of the IPD is greater than $\pi/2$. The phase shifts from the off-diagonal terms may be compared between PWC and IPCPWC. The phase shift of PWC using PW transmits of −10° and 0° degree is shown where streak noises may be seen. To examine the correlation between the streak noises and the IPD, the standard deviation of the phase shift over time and the mean of $\cos(\Delta\varphi_{0,-10})$ over time are plotted. It can be observed that the standard deviation becomes very large when the means of the cosine are negative. The results using IPCPWC are also shown. Outliers in the standard deviation plot are removed as the mean of $\cos(\Delta\varphi_{0,-10})$ is kept positive. The standard deviation is plotted on a logarithmic scale for easier comparison. IPCPWC may be used to compensate the effects of the IPD.

Figure 7:
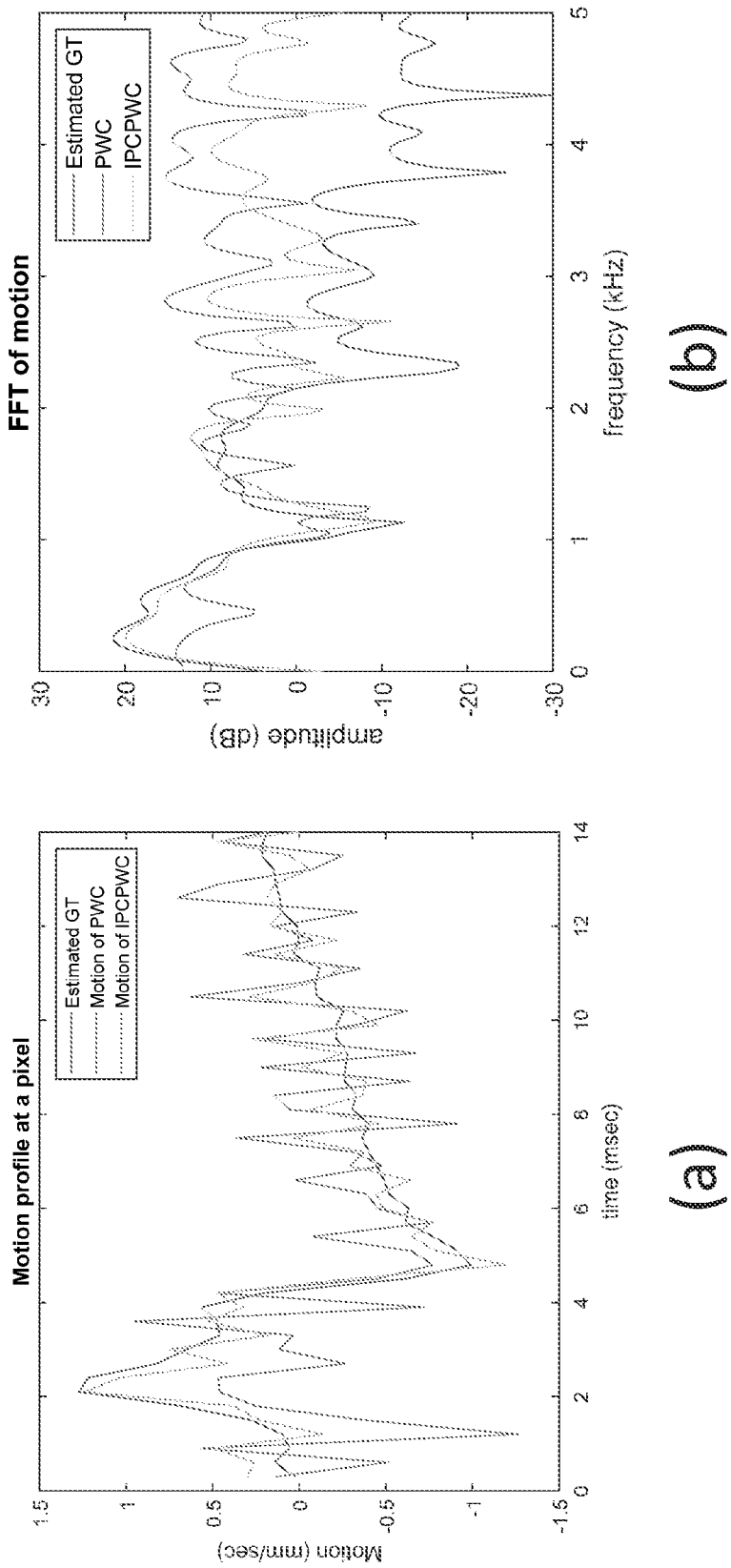
FIG. 7 are graphs of a non-limiting example of a performance comparison between PWC and IPCPWC performed using tissue-mimicking imaging phantoms.

Referring to FIG. 7, a non-limiting example is shown of a performance comparison between PWC and IPCPWC performed using the CIRS Model 039 phantoms. The SNR and jitter were used as metrics to compare the two methods. For the SNR calculation, the shear wave signal (or the ground truth) was calculated as the average of 10 independent measurements. At a pixel (x=20.1 mm, z=26.3 mm), the exemplary signals are plotted, where the ground truth, the motion profile from PWC, and the motion profile of IPCPWC are shown. The Fourier transform (FT) results of the three signals is also shown.

Figure 8A:
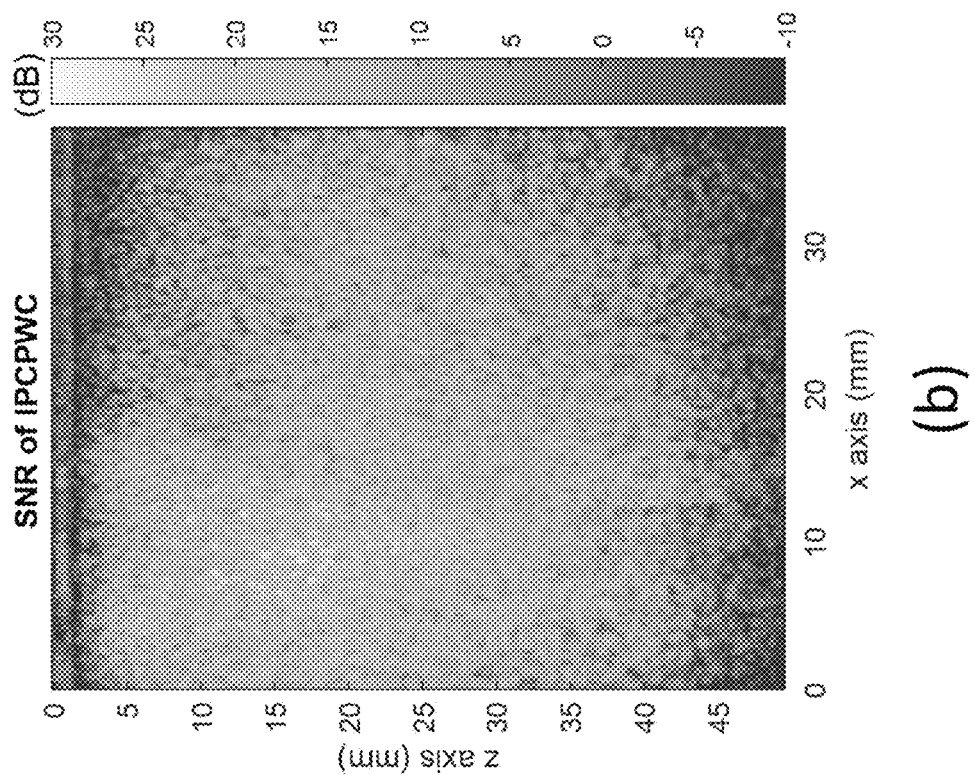
FIGS. 8A-8C are graphs of a non-limiting comparison of SNR of the motion in the xz-plane using PWC and IPCPWC.
Figure 8B:
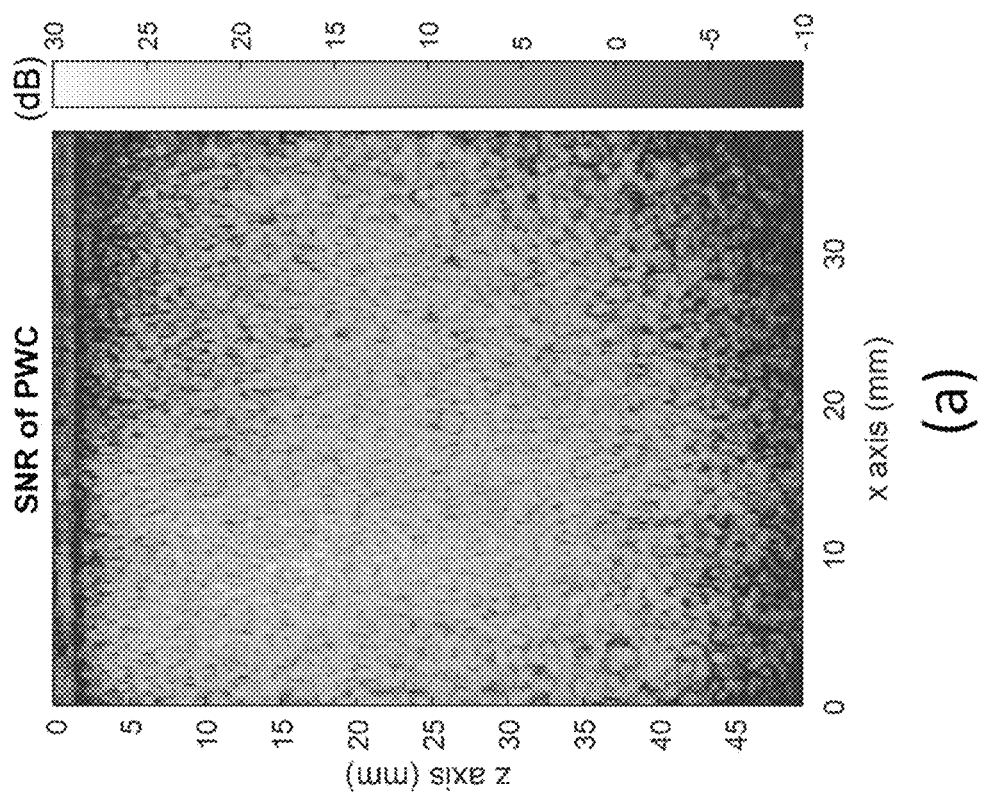
Figure 8C:
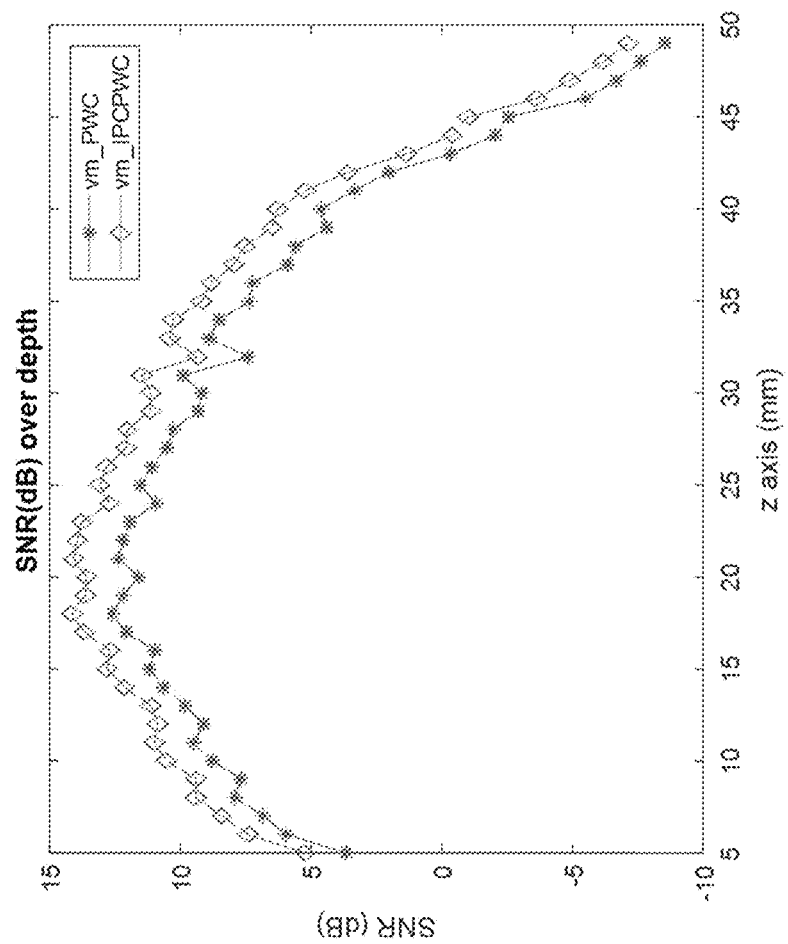

Referring to FIGS. 8A-8C, a non-limiting comparison of SNR of the motion in the xz-plane using PWC and IPCPWC are shown. IPCPWC shows better SNR. The SNR at different depths with a step of 1 mm are also shown, where the mean along the lateral dimension is calculated at a given depth.

Figures 9A, 9B:
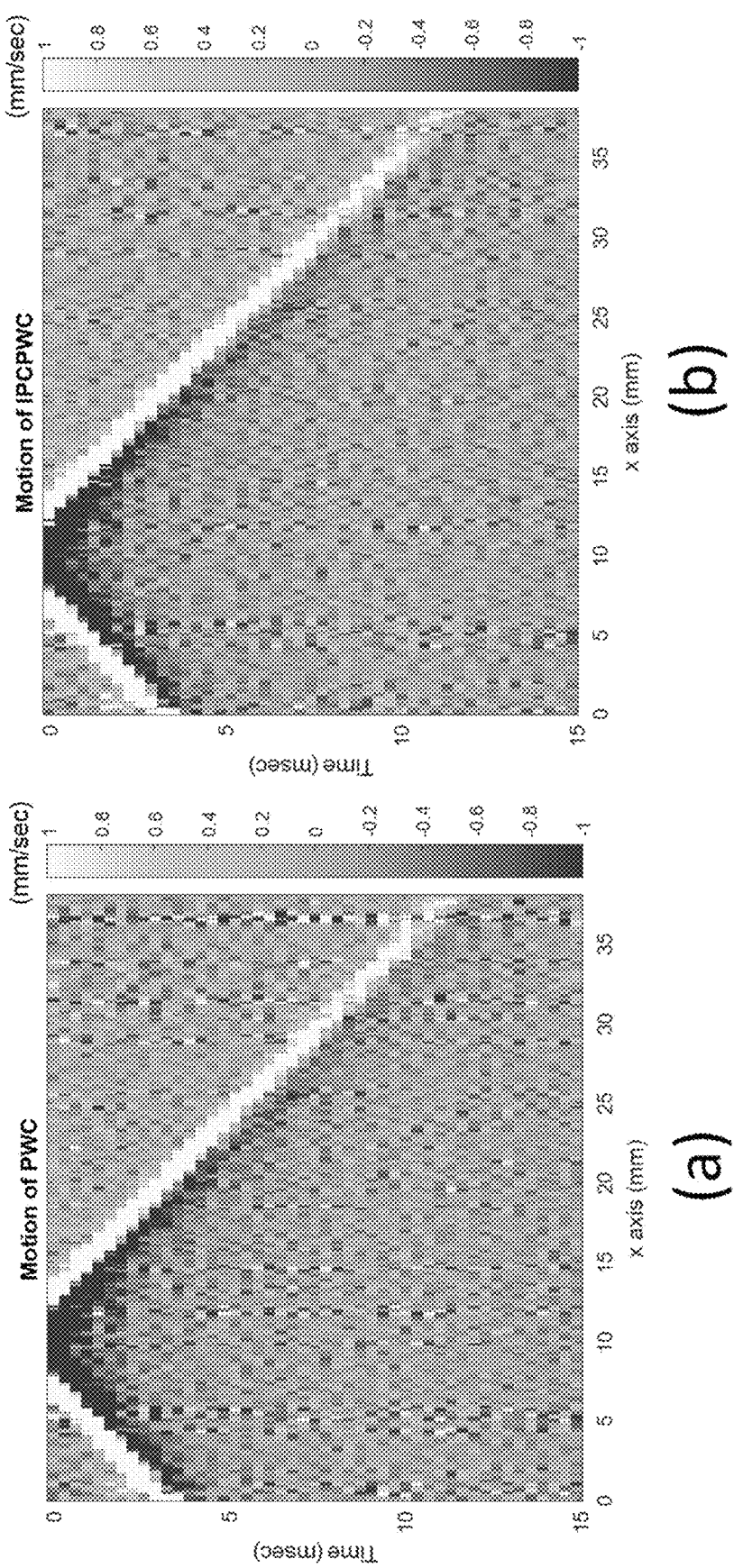
FIGS. 9A-9C are graphs of a non-limiting example of motion in the xt-plane at z=40 mm.
Figure 9C:
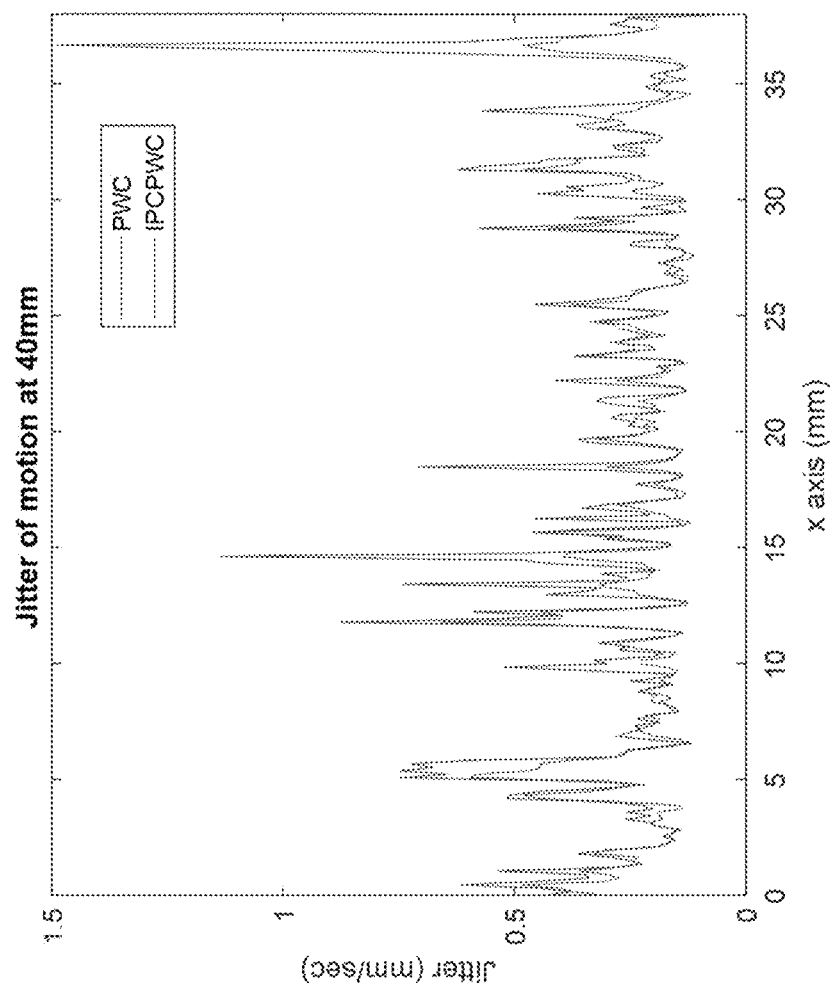

Referring to FIGS. 9A-9C, a non-limiting example of motion in the xt-plane at z=40 mm is shown. The jitter of the motion at z=40 mm is plotted and the jitter of IPCPWC reduces significantly compared to that of PWC. Table 1 summarizes the performance comparison between PWC and IPCPWC in terms of SNR and jitter. Jitter was calculated for a motion data set in which no pushing pulses were fired so that the ground truth of the motion was zero. For the SNR calculation, the push beam was generated. The spatial mean of all pixels in the xz-plane was calculated. The bottom row of the table shows the mean of four different measurements in four phantoms. Jitter was reduced by 20.0-29.4% and SNR increases by 1.65-2.62 dB when using IPCPWC.

| Nominal Stiffness | Jitter (mm/sec) | | | SNR (dB) | | |
|---|---|---|---|---|---|---|
| (Young's Modulus) | PWC | IPCPWC | Diff (%) | PWC | IPCPWC | Diff |
| 3.5 kPa | 0.34 | 0.24 | 29.4 | 1.10 | 3.72 | 2.62 |
| 10 kPa | 0.34 | 0.25 | 26.5 | 1.52 | 4.09 | 2.57 |
| 25 kPa | 0.20 | 0.16 | 20.0 | 5.93 | 7.58 | 1.65 |

-continued

| | Jitter (mm/sec) | | | SNR (dB) | | |
|---|---|---|---|---|---|---|
| Nominal Stiffness | | | Diff | | | |
| (Young's Modulus) | PWC | IPCPWC | (%) | PWC | IPCPWC | Diff |
| 45 kPa | 0.30 | 0.22 | 26.7 | 0.78 | 3.10 | 2.32 |
| Mean | 0.295 | 0.218 | 26.1 | 2.33 | 4.62 | 2.29 |

Figure 10:
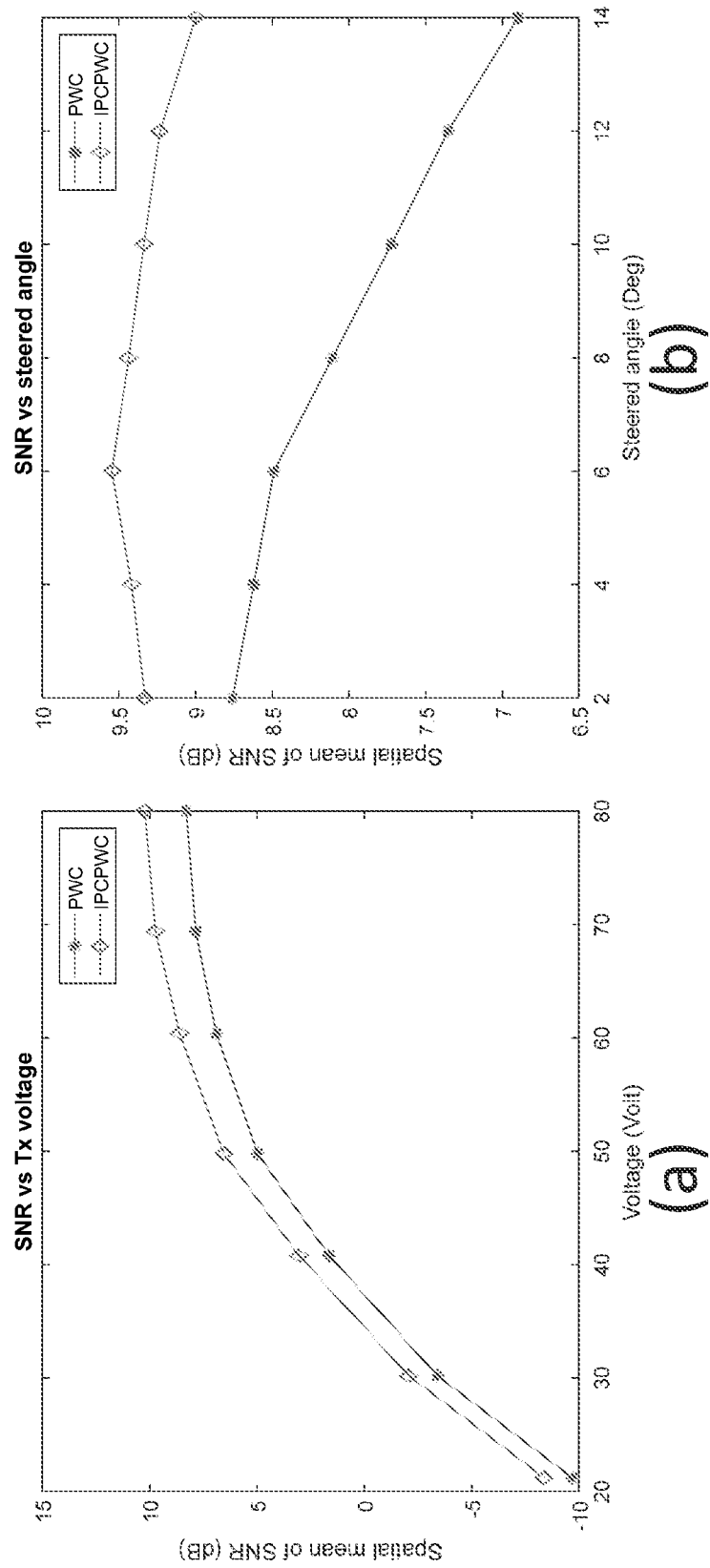
FIG. 10 are graphs of a non-limiting example of SNR versus transmitting voltage.

Referring to FIG. 10, a non-limiting example of SNR versus transmitting voltage is shown. The transmit voltages were changed from about ±20 V to ±80 V with a step of 10 V. At different voltages, the SNR of all pixels in the xz-plane were averaged. SNR versus the steered angle ($\alpha$) of plane wave is shown. Plane waves of three different angles, [$-\alpha°$, 0°, $\alpha°$] were transmitted and the spatial average of SNR in the xz-plane was plotted versus the steered angles.

Figure 11A:
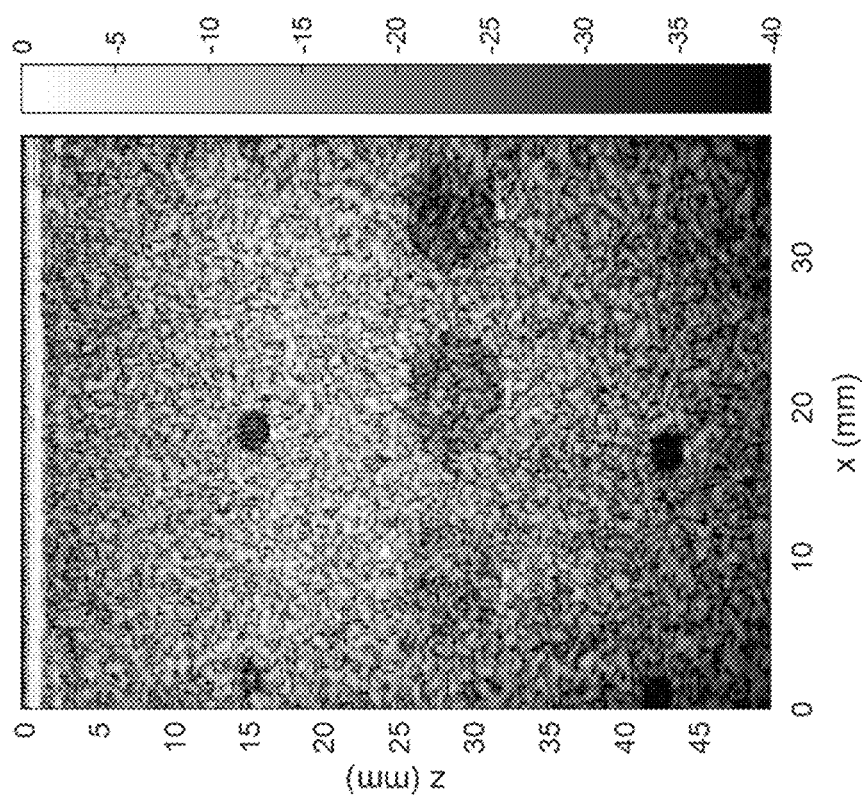
FIGS. 11A-11C are graphs of a non-limiting example SNR comparison between PWC and IPCPWC using a phantom and using angles of [−10°, 0°, 10° ].
Figures 11B, 11C:
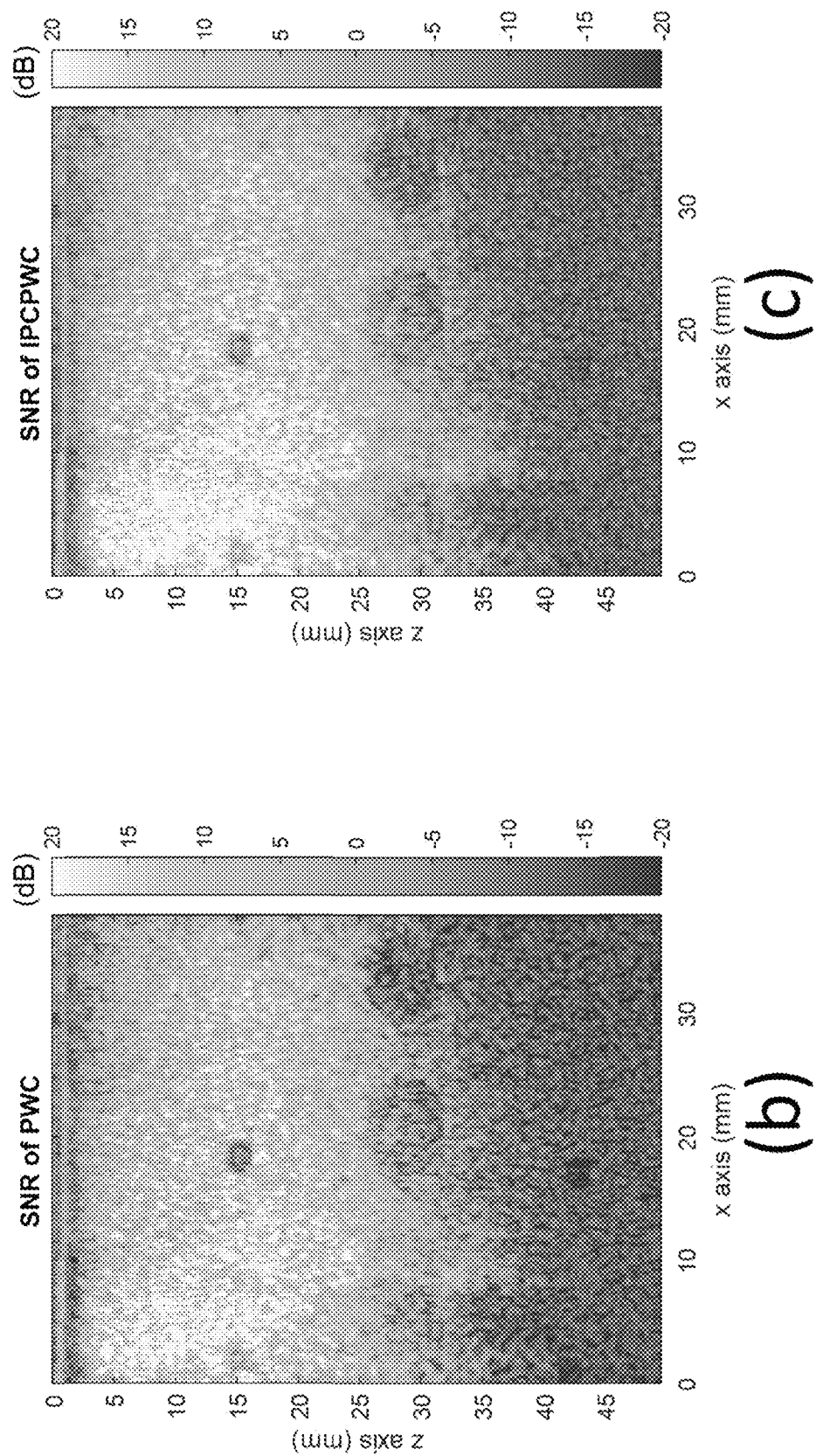

Referring to FIGS. 11A-11C, the SNR comparison between PWC and IPCPWC is shown using the CIRS Model 040GSE phantom using angles of [−10°, 0°, 10°]. The B-mode image is shown, where anechoic inclusions are located at z=15 mm and dark inclusions with −3 dB, −6 dB, and −9 dB center at the depth of 30 mm. SNR comparisons between IPC and PWC are also shown.

Figure 12A:
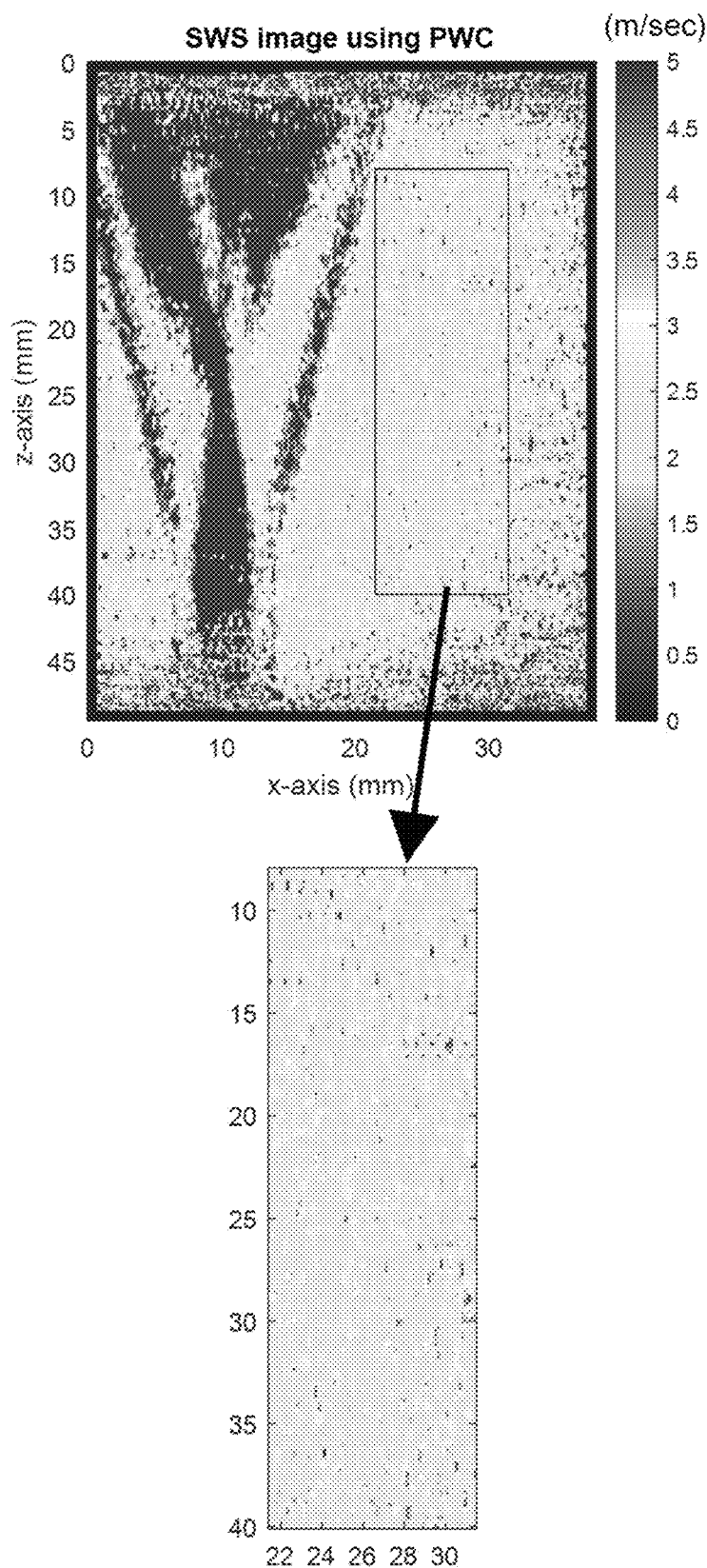
FIGS. 12A-12B are non-limiting example maps of shear wave speed on a homogeneous phantom (Young's modulus E=25 kPa) using 3 angles [−10°,0°, 10° ] using PWC or IPCPWC.
Figure 12B:
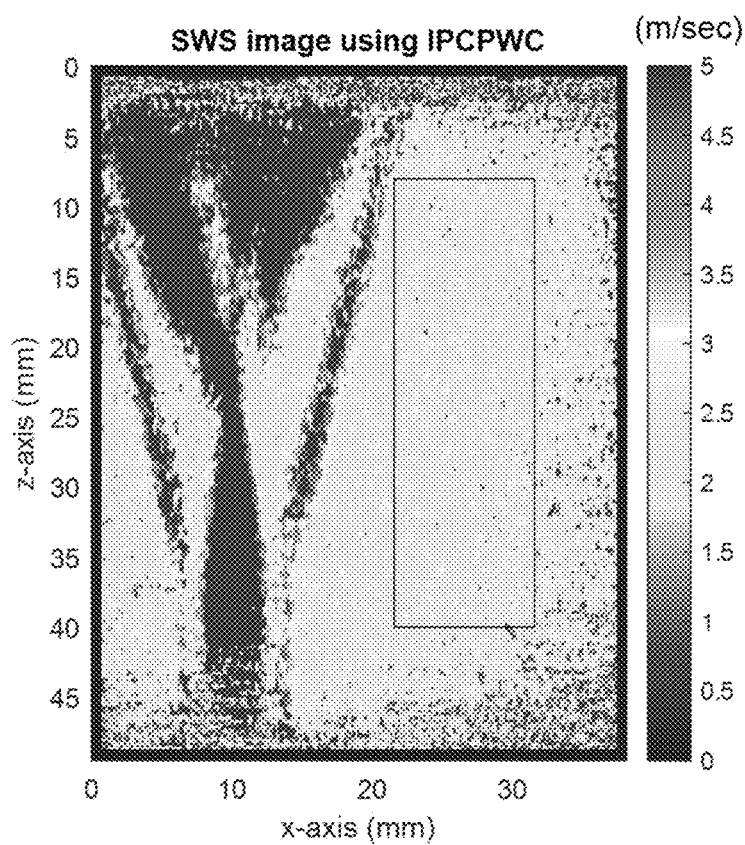
Figure 12B:
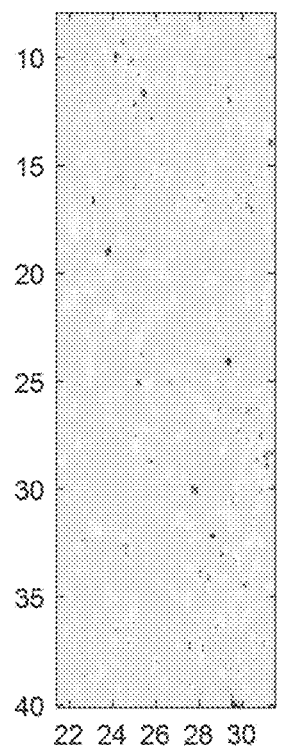

Referring to FIGS. 12A-12B, non-limiting example maps of shear wave speed on a homogeneous phantom (E=25 kPa) using 3 angles [−10°,0°, 10°] using PWC or IPCPWC are shown.

Figures 4A, 4B:
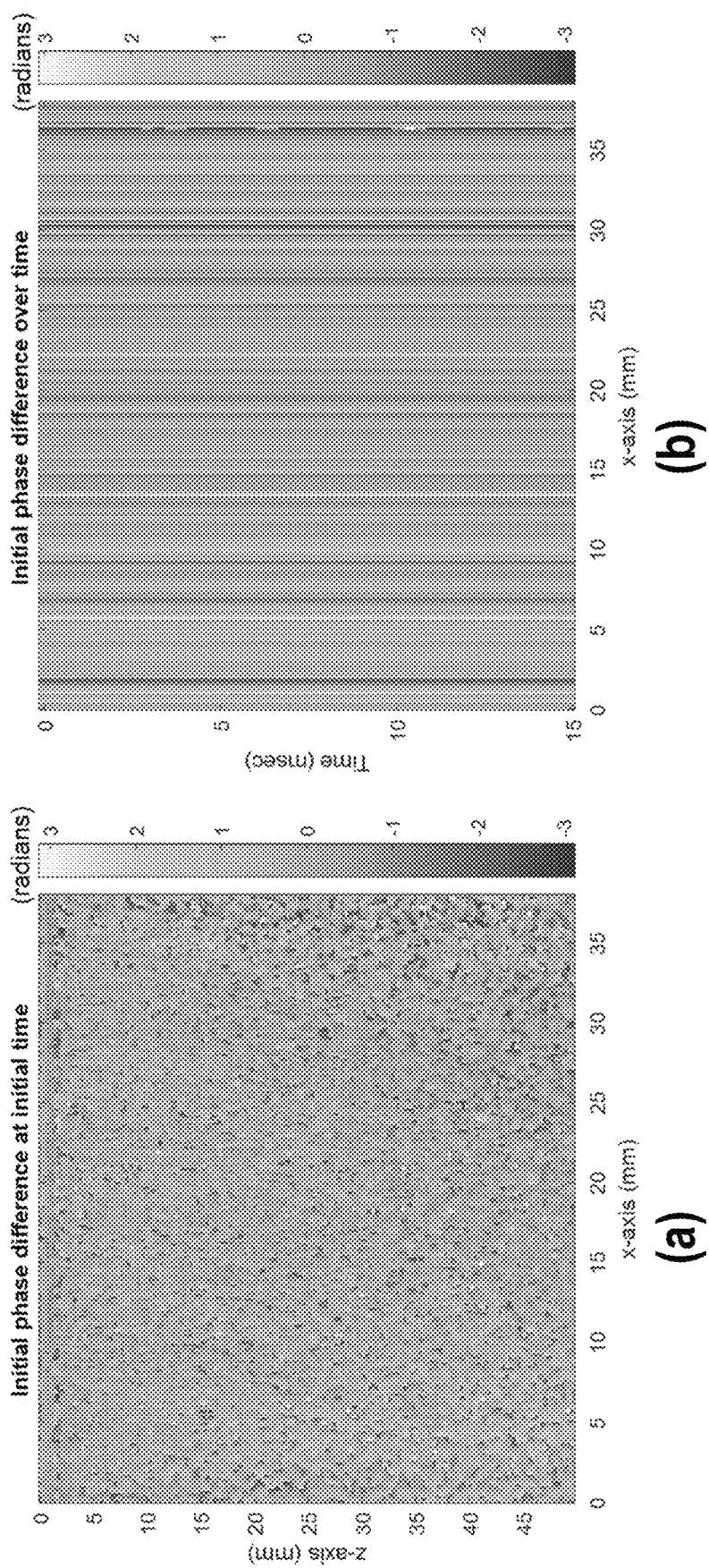
FIGS. 4A-4D are graphs of non-limiting example initial phase difference data.
Figures 4C, 4D:
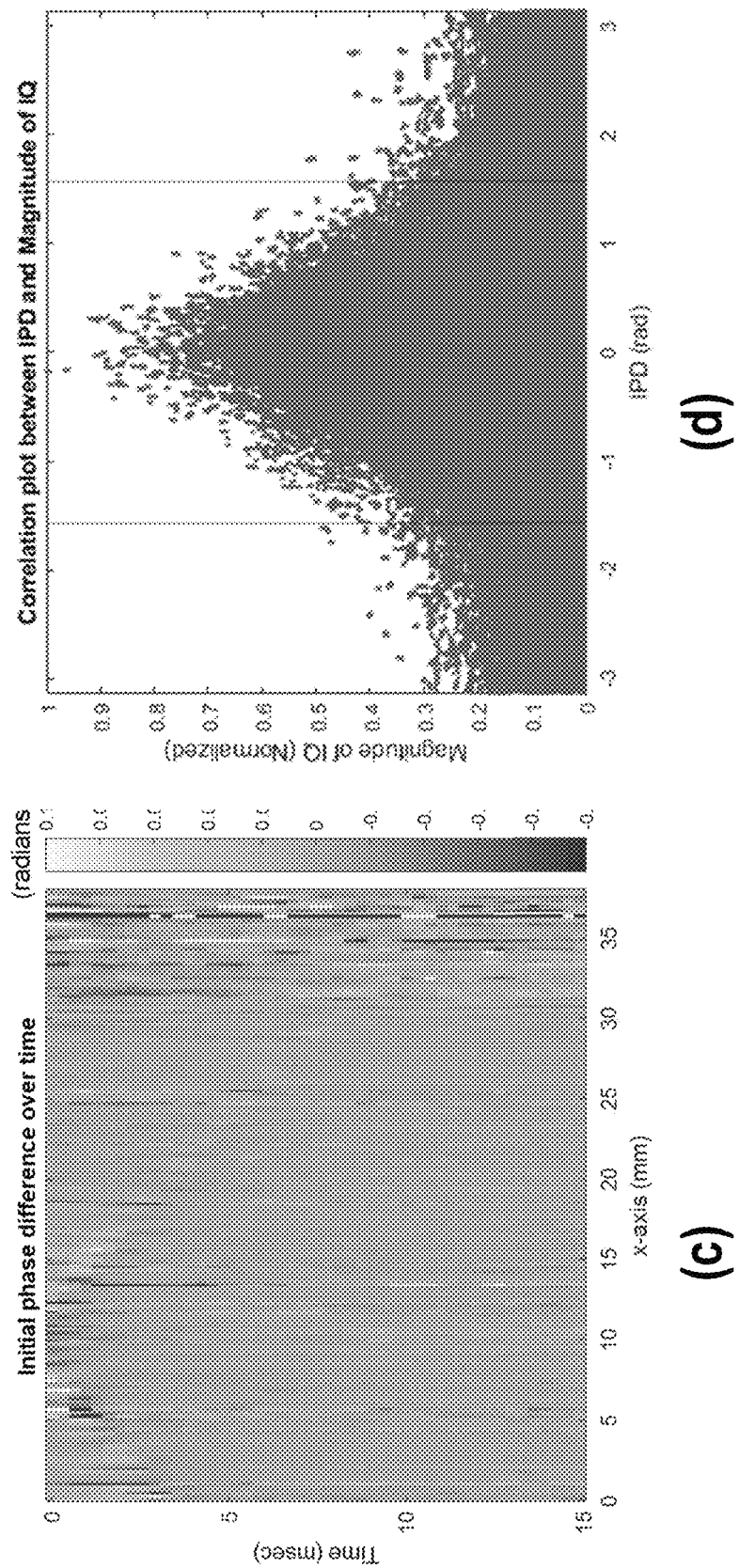
Figure 13:
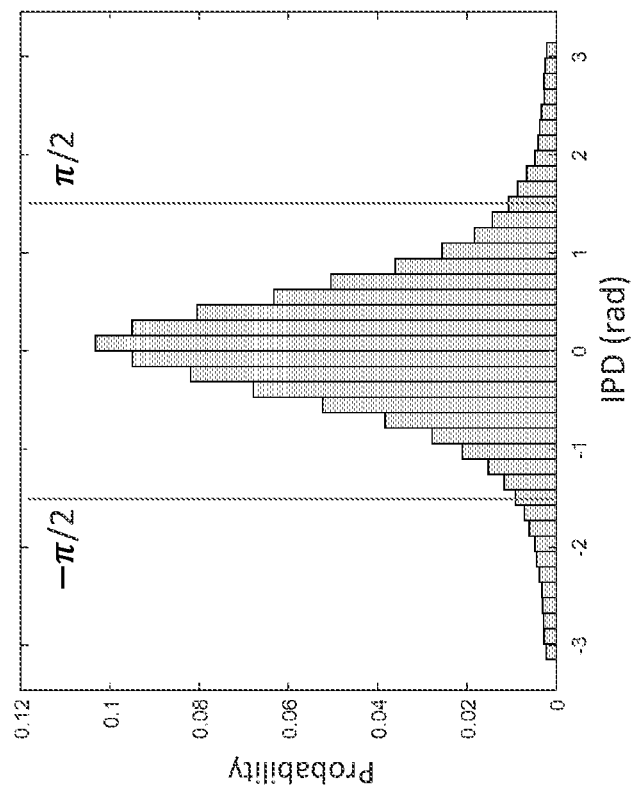
FIG. 13 are non-limiting example histograms of the IPD using the pixels of FIG. 4D.
Figure 13:
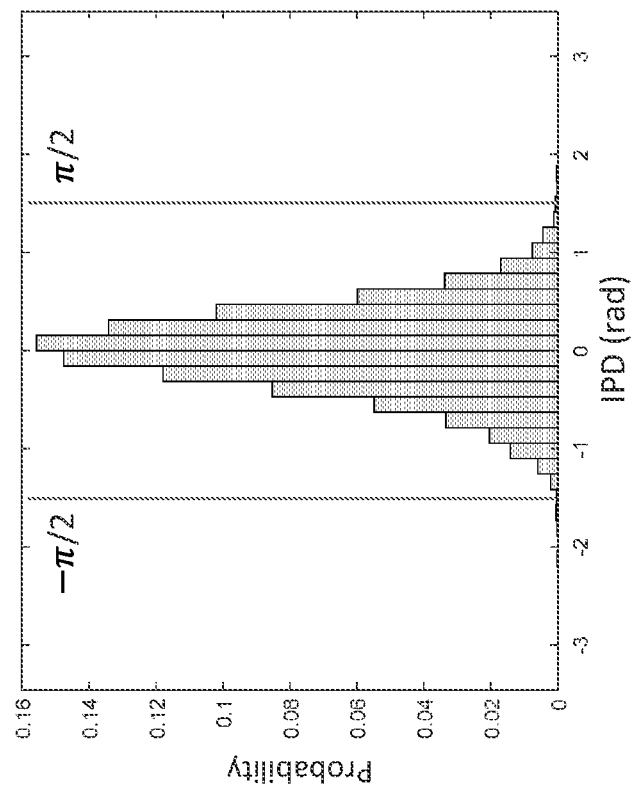

Referring to FIG. 13, non-limiting example histograms of the IPD using the pixels of FIG. 4D. Pixels of which the magnitude of IQ is larger than 0.2, and pixels of which the magnitude of IQ is less than 0.2 were used. Lines represent $-\pi/2$ and $\pi/2$ thresholds.

Figure 14:
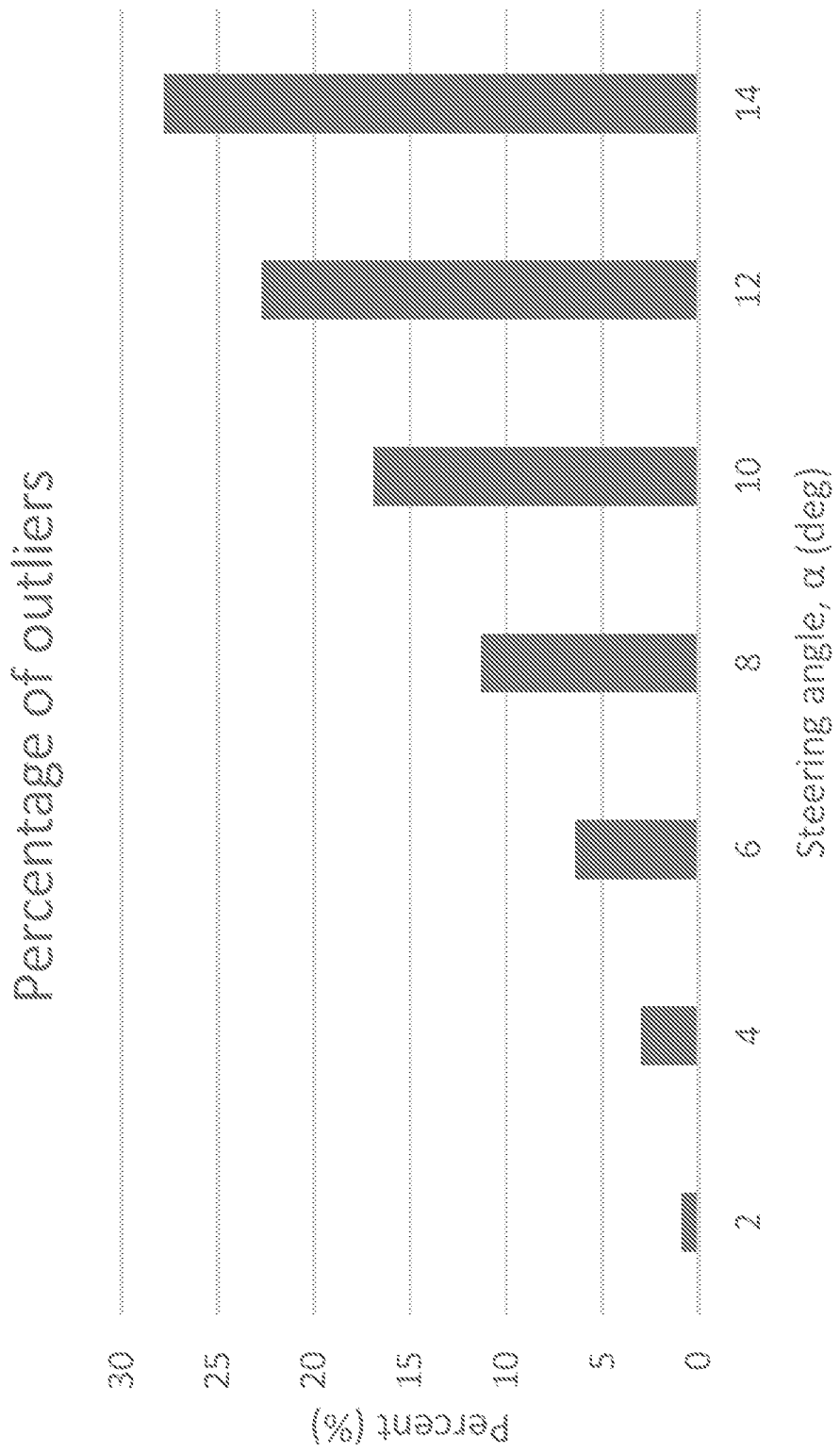
FIG. 14 graphs of a non-limiting example percentage of the pixels of which the absolute value of the initial phase difference is larger than $\pi/2$ versus steering angles.

Referring to FIG. 14, graphs of a non-limiting example percentage of the pixels of which the absolute value of the initial phase difference is larger than $\pi/2$ versus steering angles are shown. Plane wave transmissions with three angles of [$-\alpha$, 0, $\alpha$] are used. The initial phase difference between the transmits with $-\alpha$ and $\alpha$ degrees. The pixels within a ROI (lateral size of [11.8×26.1] mm, axial size of [5×49.7] mm) were calculated.

In some configurations, the systems and methods may be used to correct PWC when calculating the phase shift between two consecutive images of PWC. Unless the absolute value of IPD between two transmissions with different angles is less than $\pi/2$, the error in phase shift estimation occurs. IPCPWC compensates the initial phase of a transmit by the average value of two initial phases of two consecutive transmits with the same angle. This makes the IPD zero to ensure that the IPD is less than $\pi/2$. In non-limiting example phantom studies, SNR increases by 1.65-2.62 dB compared to PWC using the CIRS Model 039 phantoms.

In PWC, the phase shift estimation according to Eq. (8) can be considered as the weighted sum of each phase shift of the upper triangular terms of a matrix of FIG. 3. The weights of diagonal terms are the magnitude of IQ of $A_n A_n$. This can be interpreted as the pixels with strong echoes have higher weights. For the off-diagonal terms, $2\cos(\Delta\varphi_{nm})$ is multiplied by $A_n A_m$. Multiplication of 2 may be used because a pair of off-diagonal terms is summed. The cos ($\Delta\varphi_{nm}$) term is used in PWC and IPCPWC of Eq. (18) does not include this. In some configurations, the weights of the off-diagonal terms in PWC are affected by the IPD. As $|\Delta\varphi_{nm}|$ approaches $\pi/2$ (i.e. $\cos(\Delta\varphi_{nm})\approx 0$), the weight of $2\cos(\Delta\varphi_{nm})\cdot A_n A_m$ goes to zero regardless of the magnitude of IQ. IPCPWC has a more consistent weighting scheme than PWC because IPCPWC's weights may be determined by only the magnitude of IQ.

Motion estimation may have an impact on the computation of shear wave speed (SWS) maps. In a non-limiting example, SWS maps were reconstructed using the elasticity phantom (Model 039, E=25 kPa). The local estimation of the shear wave speed performed by using a one-dimensional time-of-flight algorithm. The time-of-flight $\Delta t$ was estimated by a cross-correlation between the motion profile at location x and at locations x±$\Delta$x. The $\Delta$x has been set at 0.75 mm and two time-of-flights are calculated and averaged. A 5×5 spatial Gaussian filter (MATLAB function: fspecial and imfilter) and temporal FIR lowpass filter (filter taps: 5, cutoff frequency: 1000 Hz, MATLAB function: firls and filtfilt) were applied to the motion data to increase SNR of shear wave displacement. Noise reduction in SWS thanks to IPCPWC can be seen, especially in the square black region-of-interest (ROI). The mean of standard deviation of PWC and IPCPWC within the ROI are 2.44±0.34 m/s and 2.45±0.29 m/s, respectively.

The magnitude of the IPD may be inversely correlated with the magnitude of IQ such that the dark region in B-mode images may be more likely to have more errors in phase shift estimation due to the large IPD. The dark inclusions at the axial depth of 30 mm in the non-limiting examples demonstrate lower SNR than the background. The histograms of the pixels were plotted and divided into two groups of "A" and "B": "A" group was the pixels of which the normalized magnitude of IQ is less than 0.2 and the rest of the pixels were in "B" group. The "A" group were considered as dark pixels and the IPDs extend over the $\pi/2$ threshold. The "B" group showed less pixels outside the thresholds. The dark pixels may be more likely to be affected by side-lobes and their phases may be more easily corrupted by those of the neighboring brighter pixels. Low scattering amplitude may also lead to the phase of a pixel being ill-defined.

The magnitude of IPD is also correlated with the steering angles of PW transmits. In some configurations, the ratio of the pixels of which the absolute value of IPD is larger than $\pi/2$ to the total pixels within an ROI may be determined. IPD may be calculated using the first and second PWC images using Eq. (9). In a non-limiting example, the ROI was positioned at the center in x-axis with the width of [11.8 mm, 26.1 mm] and the height of [5 mm, 49.7 mm] to ensure the ROI was covered by all angled transmits. Plane wave transmissions with three angles of [$-\alpha$, 0, $\alpha$] were used with the different a from 2° to 14° with a step of 2°. IPD between the transmits with $-\alpha$ and $\alpha$ degrees is calculated. The percentage was linearly proportional to the steering angle of PW.

Conventional plane wave compounding (PWC) causes a motion estimation error at some pixels, where the absolute value of the initial phase difference between two PW transmissions are larger than $\pi/2$. To mitigate or reduce this error, Initial-Phase-Compensated PWC (IPCPWC) may be used, which makes the initial phase difference zero by compensating the initial phase of IQ signals of PW transmits. Phantom studies show that IPCPWC has better SNR (increased by 1.65-2.62 dB) and lower jitter (reduced by 20.0-29.4%) compared to PWC in motion data. The comparison was performed with different parameters of experiments such as transmit voltages and steering angles and the tendency that IPCPWC outperforms PWC is consistent with any changes to the parameters.

Figure 15:
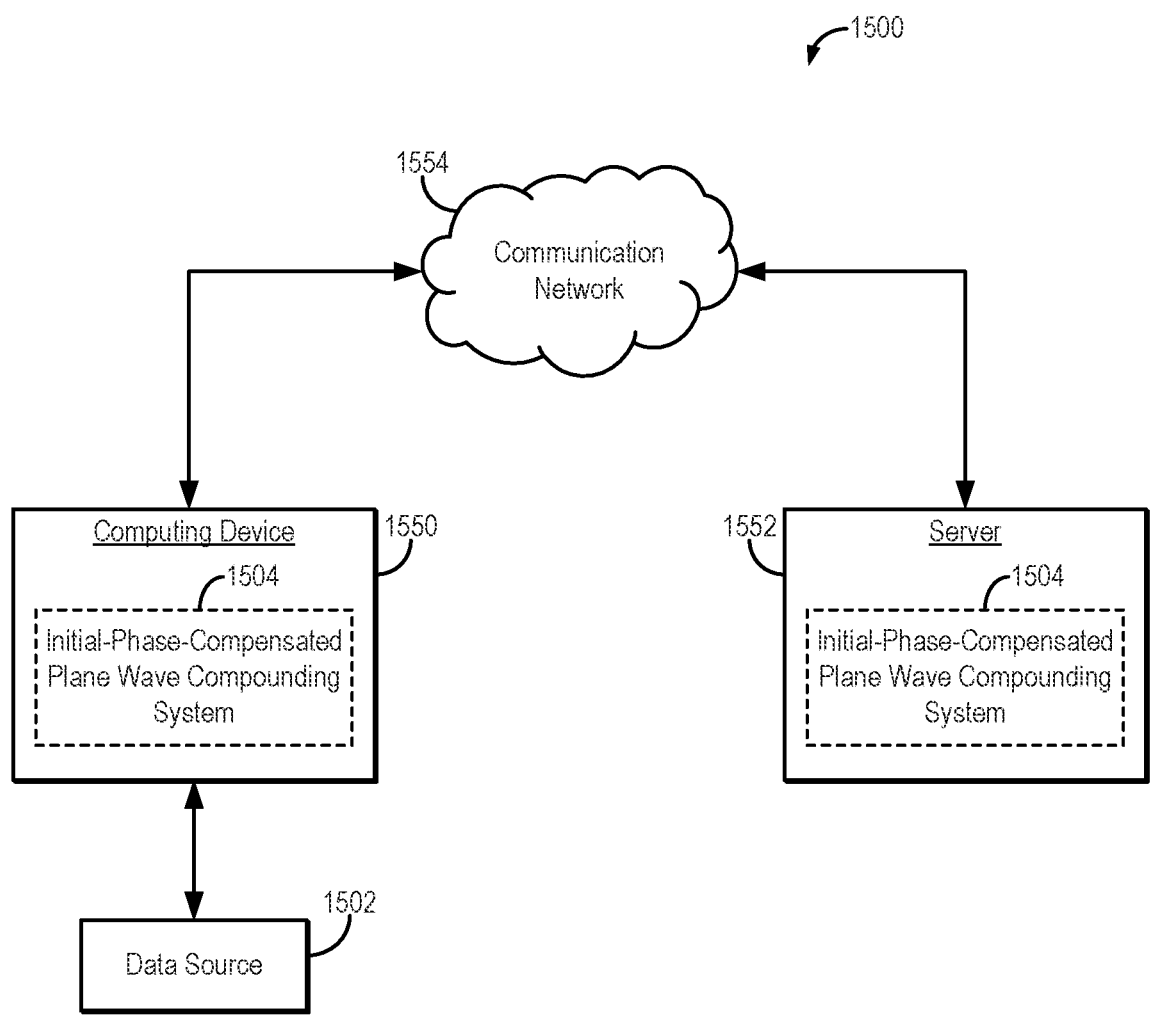
FIG. 15 is a block diagram of an example computer system configured to perform initial-phase-compensated plane wave compounding in accordance with some embodiments described in the present disclosure.

Referring now to FIG. 15, an example of a system 1500 for initial-phase-compensated plane wave compounding in accordance with some embodiments of the systems and methods described in the present disclosure is shown. As shown in FIG. 15, a computing device 1550 can receive one or more types of data (e.g., ultrasound data) from data source 1502. In some embodiments, computing device 1550 can execute at least a portion of an initial-phase-compensated plane wave compounding system 1504 to generate images from ultrasound data received from the data source 1502.

Additionally or alternatively, in some embodiments, the computing device 1550 can communicate information about data received from the data source 1502 to a server 1552 over a communication network 1554, which can execute at least a portion of the initial-phase-compensated plane wave compounding system 1504. In such embodiments, the server 1552 can return information to the computing device 1550 (and/or any other suitable computing device) indicative of an output of the initial-phase-compensated plane wave compounding system 1504.

In some embodiments, computing device 1550 and/or server 1552 can be any suitable computing device or combination of devices, such as a desktop computer, a laptop computer, a smartphone, a tablet computer, a wearable computer, a server computer, a virtual machine being executed by a physical computing device, and so on. The computing device 1550 and/or server 1552 can also reconstruct images from the data.

In some embodiments, data source 1502 can be any suitable source of data (e.g., measurement data, images reconstructed from measurement data, processed image data), such as an ultrasound imaging system, another computing device (e.g., a server storing measurement data, images reconstructed from measurement data, processed image data), and so on. In some embodiments, data source 1502 can be local to computing device 1550. For example, data source 1502 can be incorporated with computing device 1550 (e.g., computing device 1550 can be configured as part of a device for measuring, recording, estimating, acquiring, or otherwise collecting or storing data). As another example, data source 1502 can be connected to computing device 1550 by a cable, a direct wireless link, and so on. Additionally or alternatively, in some embodiments, data source 1502 can be located locally and/or remotely from computing device 1550, and can communicate data to computing device 1550 (and/or server 1552) via a communication network (e.g., communication network 1554).

In some embodiments, communication network 1554 can be any suitable communication network or combination of communication networks. For example, communication network 1554 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), other types of wireless network, a wired network, and so on. In some embodiments, communication network 1554 can be a local area network, a wide area network, a public network (e.g., the Internet), a private or semi-private network (e.g., a corporate or university intranet), any other suitable type of network, or any suitable combination of networks. Communications links shown in FIG. 15 can each be any suitable communications link or combination of communications links, such as wired links, fiber optic links, Wi-Fi links, Bluetooth links, cellular links, and so on.

Figure 16:
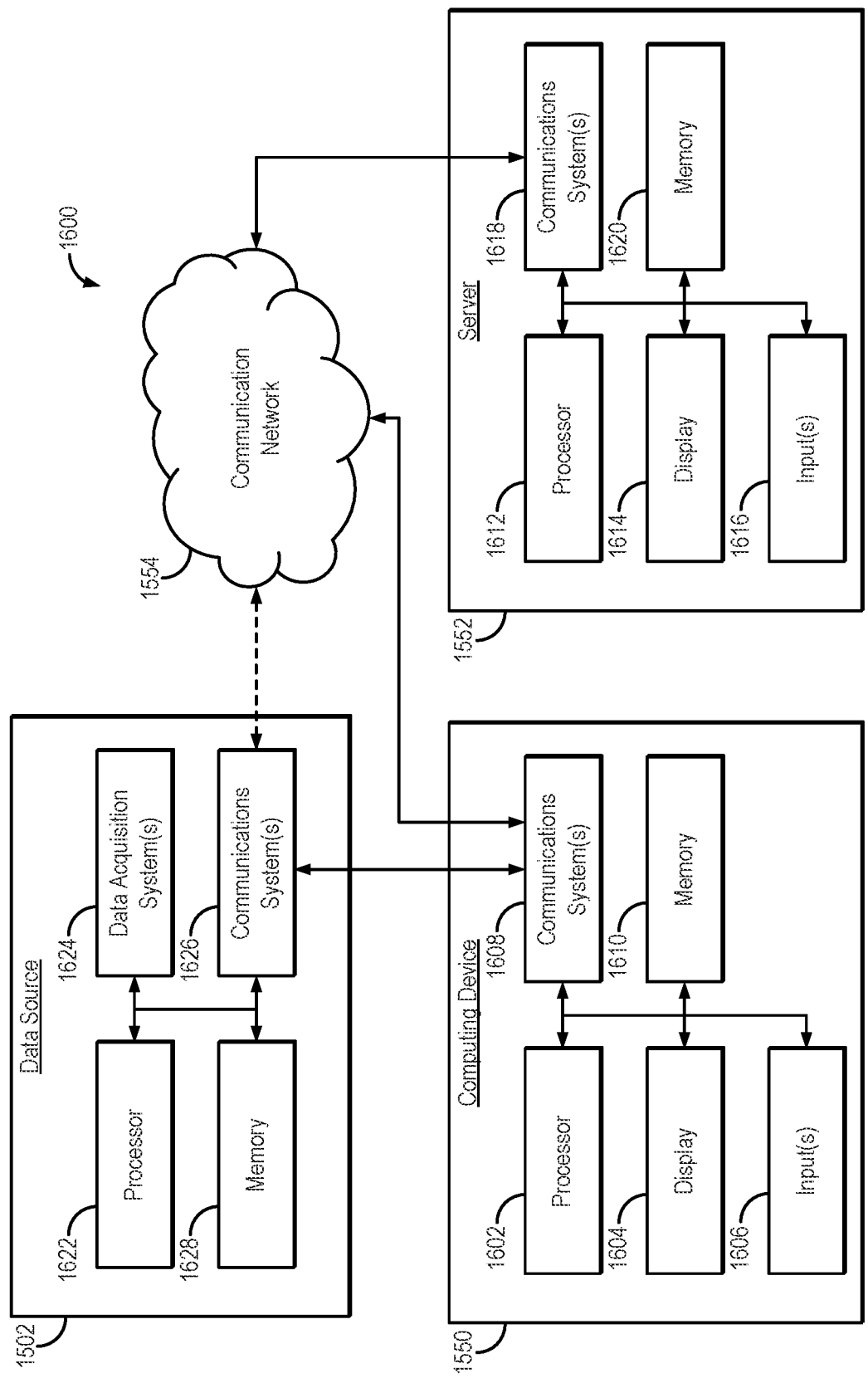
FIG. 16 is a block diagram of example components that can implement the system of FIG. 15.

Referring now to FIG. 16, an example of hardware 1600 that can be used to implement data source 1502, computing device 1550, and server 1552 in accordance with some embodiments of the systems and methods described in the present disclosure is shown. As shown in FIG. 16, in some embodiments, computing device 1550 can include a processor 1602, a display 1604, one or more inputs 1606, one or more communication systems 1608, and/or memory 1610. In some embodiments, processor 1602 can be any suitable hardware processor or combination of processors, such as a central processing unit ("CPU"), a graphics processing unit ("GPU"), and so on. In some embodiments, display 1604 can include any suitable display devices, such as a liquid crystal display ("LCD") screen, a light-emitting diode ("LED") display, an organic LED ("OLED") display, an electrophoretic display (e.g., an "e-ink" display), a computer monitor, a touchscreen, a television, and so on. In some embodiments, inputs 1606 can include any suitable input devices and/or sensors that can be used to receive user input, such as a keyboard, a mouse, a touchscreen, a microphone, and so on.

In some embodiments, communications systems 1608 can include any suitable hardware, firmware, and/or software for communicating information over communication network 1554 and/or any other suitable communication networks. For example, communications systems 1608 can include one or more transceivers, one or more communication chips and/or chip sets, and so on. In a more particular example, communications systems 1608 can include hardware, firmware, and/or software that can be used to establish a Wi-Fi connection, a Bluetooth connection, a cellular connection, an Ethernet connection, and so on.

In some embodiments, memory 1610 can include any suitable storage device or devices that can be used to store instructions, values, data, or the like, that can be used, for example, by processor 1602 to present content using display 1604, to communicate with server 1552 via communications system(s) 1608, and so on. Memory 1610 can include any suitable volatile memory, non-volatile memory, storage, or any suitable combination thereof. For example, memory 1610 can include random-access memory ("RAM"), read-only memory ("ROM"), electrically programmable ROM ("EPROM"), electrically erasable ROM ("EEPROM"), other forms of volatile memory, other forms of non-volatile memory, one or more forms of semi-volatile memory, one or more flash drives, one or more hard disks, one or more solid state drives, one or more optical drives, and so on. In some embodiments, memory 1610 can have encoded thereon, or otherwise stored therein, a computer program for controlling operation of computing device 1550. In such embodiments, processor 1602 can execute at least a portion of the computer program to present content (e.g., images, user interfaces, graphics, tables), receive content from server 1552, transmit information to server 1552, and so on. For example, the processor 1602 and the memory 1610 can be configured to perform the methods described herein (e.g., the method of FIG. 1).

In some embodiments, server 1552 can include a processor 1612, a display 1614, one or more inputs 1616, one or more communications systems 1618, and/or memory 1620. In some embodiments, processor 1612 can be any suitable hardware processor or combination of processors, such as a CPU, a GPU, and so on. In some embodiments, display 1614 can include any suitable display devices, such as an LCD screen, LED display, OLED display, electrophoretic display, a computer monitor, a touchscreen, a television, and so on. In some embodiments, inputs 1616 can include any suitable input devices and/or sensors that can be used to receive user input, such as a keyboard, a mouse, a touchscreen, a microphone, and so on.

In some embodiments, communications systems 1618 can include any suitable hardware, firmware, and/or software for communicating information over communication network 1554 and/or any other suitable communication networks. For example, communications systems 1618 can include one or more transceivers, one or more communication chips and/or chip sets, and so on. In a more particular example, communications systems 1618 can include hardware, firmware, and/or software that can be used to establish a Wi-Fi connection, a Bluetooth connection, a cellular connection, an Ethernet connection, and so on.

In some embodiments, memory 1620 can include any suitable storage device or devices that can be used to store instructions, values, data, or the like, that can be used, for example, by processor 1612 to present content using display 1614, to communicate with one or more computing devices 1550, and so on. Memory 1620 can include any suitable volatile memory, non-volatile memory, storage, or any suitable combination thereof. For example, memory 1620 can include RAM, ROM, EPROM, EEPROM, other types of volatile memory, other types of non-volatile memory, one or more types of semi-volatile memory, one or more flash drives, one or more hard disks, one or more solid state drives, one or more optical drives, and so on. In some embodiments, memory 1620 can have encoded thereon a server program for controlling operation of server 1552. In such embodiments, processor 1612 can execute at least a portion of the server program to transmit information and/or content (e.g., data, images, a user interface) to one or more computing devices 1550, receive information and/or content from one or more computing devices 1550, receive instructions from one or more devices (e.g., a personal computer, a laptop computer, a tablet computer, a smartphone), and so on.

In some embodiments, the server 1552 is configured to perform the methods described in the present disclosure. For example, the processor 1612 and memory 1620 can be configured to perform the methods described herein (e.g., the method of FIG. 1).

In some embodiments, data source 1502 can include a processor 1622, one or more data acquisition systems 1624, one or more communications systems 1626, and/or memory 1628. In some embodiments, processor 1622 can be any suitable hardware processor or combination of processors, such as a CPU, a GPU, and so on. In some embodiments, the one or more data acquisition systems 1624 are generally configured to acquire data, images, or both, and can include an MRI system. Additionally or alternatively, in some embodiments, the one or more data acquisition systems 1624 can include any suitable hardware, firmware, and/or software for coupling to and/or controlling operations of an MRI system. In some embodiments, one or more portions of the data acquisition system(s) 1624 can be removable and/or replaceable.

Note that, although not shown, data source 1502 can include any suitable inputs and/or outputs. For example, data source 1502 can include input devices and/or sensors that can be used to receive user input, such as a keyboard, a mouse, a touchscreen, a microphone, a trackpad, a trackball, and so on. As another example, data source 1502 can include any suitable display devices, such as an LCD screen, an LED display, an OLED display, an electrophoretic display, a computer monitor, a touchscreen, a television, etc., one or more speakers, and so on.

In some embodiments, communications systems 1626 can include any suitable hardware, firmware, and/or software for communicating information to computing device 1550 (and, in some embodiments, over communication network 1554 and/or any other suitable communication networks). For example, communications systems 1626 can include one or more transceivers, one or more communication chips and/or chip sets, and so on. In a more particular example, communications systems 1626 can include hardware, firmware, and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 1628 can include any suitable storage device or devices that can be used to store instructions, values, data, or the like, that can be used, for example, by processor 1622 to control the one or more data acquisition systems 1624, and/or receive data from the one or more data acquisition systems 1624; to generate images from data; present content (e.g., data, images, a user interface) using a display: communicate with one or more computing devices 1550; and so on. Memory 1628 can include any suitable volatile memory, non-volatile memory, storage, or any suitable combination thereof. For example, memory 1628 can include RAM, ROM, EPROM, EEPROM, other types of volatile memory, other types of non-volatile memory, one or more types of semi-volatile memory, one or more flash drives, one or more hard disks, one or more solid state drives, one or more optical drives, and so on. In some embodiments, memory 1628 can have encoded thereon, or otherwise stored therein, a program for controlling operation of data source 1502. In such embodiments, processor 1622 can execute at least a portion of the program to generate images, transmit information and/or content (e.g., data, images, a user interface) to one or more computing devices 1550, receive information and/or content from one or more computing devices 1550, receive instructions from one or more devices (e.g., a personal computer, a laptop computer, a tablet computer, a smartphone, etc.), and so on.

In some embodiments, any suitable computer-readable media can be used for storing instructions for performing the functions and/or processes described herein. For example, in some embodiments, computer-readable media can be transitory or non-transitory. For example, non-transitory computer-readable media can include media such as magnetic media (e.g., hard disks, floppy disks), optical media (e.g., compact discs, digital video discs, Blu-ray discs), semiconductor media (e.g., RAM, flash memory, EPROM, EEPROM), any suitable media that is not fleeting or devoid of any semblance of permanence during transmission, and/or any suitable tangible media. As another example, transitory computer-readable media can include signals on networks, in wires, conductors, optical fibers, circuits, or any suitable media that is fleeting and devoid of any semblance of permanence during transmission, and/or any suitable intangible media.

As used herein in the context of computer implementation, unless otherwise specified or limited, the terms "component," "system," "module," "framework," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

In some implementations, devices or systems disclosed herein can be utilized or installed using methods embodying aspects of the disclosure. Correspondingly, description herein of particular features, capabilities, or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, discussion herein of any method of manufacturing or using a particular device or system, including installing the device or system, is intended to inherently include disclosure, as embodiments of the disclosure, of the utilized features and implemented capabilities of such device or system.

The present disclosure has described one or more preferred embodiments, and it should be appreciated that many equivalents, alternatives, variations, and modifications, aside from those expressly stated, are possible and within the scope of the invention.

The invention claimed is:

1. A method for ultrasound plane wave compounding imaging, comprising:
   a) accessing ultrasound plane wave time series data with a computer system, wherein the ultrasound plane wave time series data were acquired from a region of a subject and comprise ultrasound plane wave data acquired for a plurality of different transmission angles at each of a plurality of time points;
   b) selecting a first data set from the ultrasound plane wave time series data corresponding to ultrasound plane wave data acquired for the plurality of the different transmission angles at a first time point;
   c) selecting a second data set from the ultrasound plane wave time series data corresponding to ultrasound plane wave data acquired for the plurality of the different transmission angles at a second time point that is subsequent to the first time point;
   d) calculating with the computer system for each of the plurality of different transmission angles, an initial phase angle mean value between ultrasound plane wave data in the first data set and the second data set corresponding to a common one of the plurality of the different transmission angles;
   e) generating initial-phase-compensated plane wave data by adjusting the ultrasound plane wave data in the first data set and the second data set using the initial phase angle mean values calculated for each of the plurality of different transmission angles;
   f) constructing phase-compensated images from the initial-phase-compensated plane wave data, wherein the phase-compensated images depict the region of the subject at the first time point and the second time point.

2. The method of claim 1, wherein adjusting the ultrasound plane wave data in the first data set and the second data set includes subtracting the initial phase angle mean value calculated for a given transmission angle from a phase value of the ultrasound plane wave data in the first data set and the second data set corresponding to the given transmission angle.

3. The method of claim 1, further comprising repeating steps b)-f) for successive pairs of time points in the plurality of time points, thereby constructing a time series of phase-compensated images.

4. The method of claim 1, wherein constructing phase-compensated images from the initial-phase-compensated plane wave data includes coherently combining initial-phase-compensated ultrasound plane wave data in the first data set to generate a phase-compensated image depicting the region of the subject at the first time point, and coherently combining initial-phase-compensated ultrasound plane wave data in the second data set to generate a phase-compensated image depicting the region of the subject at the second time point.

5. The method of claim 1, wherein the ultrasound plane wave data in the ultrasound plane wave time series data comprise one of in-phase quadrature (IQ) data or radio frequency (RF) signal data.

6. The method of claim 1, wherein accessing the ultrasound plane wave time series data with the computer system comprises:
   operating the computer system to control an ultrasound system to generate a series of angled wave emissions corresponding to the plurality of different transmission angles over a duration of time corresponding to the plurality of time points; and
   controlling the ultrasound system with the computer system to acquire the ultrasound plane wave data in response thereto.

7. The method of claim 1, wherein one or more shear waves were induced in the region of the subject prior to acquiring the ultrasound plane wave data such that the ultrasound plane wave times series data are indicative of shear wave motion occurring in the region of the subject.

8. The method of claim 7, further comprising estimating motion data from the phase-compensated images, wherein the motion data are indicative of the shear wave motion of the one or more shear waves in the region of the subject.

9. The method of claim 8, wherein the motion data are estimated from a phase shift between the first time point and the second time point, wherein the phase shift comprises:

$$\delta\theta = ang(\bar{S} \times \bar{R}^*)$$
$$= ang\left(\frac{1}{N^2}\left(\sum_{n=1}^{N} A_n A_n + \sum_{m>n} 2A_n A_m\right) e^{i\omega_c \delta t}\right)$$
$$= \omega_c \delta t.$$

wherein $\delta\theta$ represents the phase shift, m and n are different ones of the plurality of transmission angles, t is time along a depth dimension, $A_n$ is an amplitude of a signal in the ultrasound plane wave data, $\omega_c$ is a center frequency of a carrier signal, and $\delta t$ represents time delay.

10. The method of claim 8, wherein the motion data are estimated from a phase shift between the first time point and the second time point, wherein the phase shift comprises $$\delta\theta = ang(\bar{S} \times \bar{R}^*) = \omega_c \delta t$$

wherein δθ represents the phase shift, t is time along a depth dimension, $\omega_c$ is a center frequency of a carrier signal, and δt is a time delay.

11. A system for ultrasound plane wave compounding imaging, comprising:
an ultrasound imaging system configured to acquire plane wave time series data for plane wave compounding imaging;
a computer system in communication with the ultrasound imaging system and configured to:
i) access ultrasound plane wave time series data acquired with the ultrasound imaging system, wherein the ultrasound plane wave time series data were acquired from a region of a subject and comprise ultrasound plane wave data acquired for a plurality of different transmission angles at each of a plurality of time points;
ii) select a first data set from the ultrasound plane wave time series data corresponding to ultrasound plane wave data acquired for the plurality of the different transmission angles at a first time point;
iii) select a second data set from the ultrasound plane wave time series data corresponding to ultrasound plane wave data acquired for the plurality of the different transmission angles at a second time point that is subsequent to the first time point;
iv) calculate for each of the plurality of different transmission angles an initial phase angle mean value between ultrasound plane wave data in the first data set and the second data set corresponding to a common one of the plurality of the different transmission angles;
v) generate initial-phase-compensated plane wave data by adjusting the ultrasound plane wave data in the first data set and the second data set using the initial phase angle mean values calculated for each of the plurality of different transmission angles;
vi) construct phase-compensated images from the initial-phase-compensated plane wave data, wherein the phase-compensated images depict the region of the subject at the first time point and the second time point.

12. The system of claim 11, wherein the computer system is further configured to adjust the ultrasound plane wave data in the first data set and the second data set by subtracting the initial phase angle mean value calculated for a given transmission angle from a phase value of the ultrasound plane wave data in the first data set and the second data set corresponding to the given transmission angle.

13. The system of claim 11, wherein the computer system is further configured to repeat steps ii)-vi) for successive pairs of time points in the plurality of time points, thereby constructing a time series of phase-compensated images.

14. The system of claim 11, wherein the computer system is further configured to construct the phase-compensated images from the initial-phase-compensated plane wave data by coherently combining initial-phase-compensated ultrasound plane wave data in the first data set to generate a phase-compensated image depicting the region of the subject at the first time point, and coherently combining initial-phase-compensated ultrasound plane wave data in the second data set to generate a phase-compensated image depicting the region of the subject at the second time point.

15. The system of claim 11, wherein the ultrasound plane wave data in the ultrasound plane wave time series data comprise one of in-phase quadrature (IQ) data or radio frequency (RF) signal data.

16. The system of claim 11, wherein the computer system is further configured to access the ultrasound plane wave time series data by being configured to:
control the ultrasound system to generate a series of angled wave emissions corresponding to the plurality of different transmission angles over a duration of time corresponding to the plurality of time points; and
control the ultrasound system to acquire the ultrasound plane wave data in response thereto.

17. The system of claim 11, wherein one or more shear waves were induced in the region of the subject prior to acquiring the ultrasound plane wave data such that the ultrasound plane wave times series data are indicative of shear wave motion occurring in the region of the subject.

18. The system of claim 17, wherein the computer system is further configured to estimate motion data from the phase-compensated images, wherein the motion data are indicative of the shear wave motion of the one or more shear waves in the region of the subject.

19. The system of claim 18, wherein the computer system is further configured to estimate motion data from a phase shift between the first time point and the second time point, wherein the phase shift comprises:

$$\delta\theta = ang(\bar{S} \times \bar{R}^*)$$
$$= ang\left(\frac{1}{N^2}\left(\sum_{n=1}^{N} A_n A_n + \sum_{m>n} 2A_n A_m\right)e^{i\omega_c \delta t}\right)$$
$$= \omega_c \delta t.$$

wherein δθ is the phase shift, m and n are different ones of the plurality of transmission angles, t is time along a depth dimension, $A_n$ is an amplitude of a signal in the ultrasound plane wave data, $\omega_c$ is a center frequency of a carrier signal, and δt is a time delay.

20. The system of claim 18, wherein the computer system is further configured to estimate motion data from a phase shift between the first time point and the second time point, wherein the phase shift comprises:

$$\delta\theta = ang(\bar{S} \times \bar{R}^*) = \omega_c \delta t$$

wherein δθ represents the phase shift, t is time along a depth dimension, $\omega_c$ is a center frequency of a carrier signal, and δt is a time delay.

* * * * *

UNITED STATES PATENT AND TRADEMARK OFFICE
CERTIFICATE OF CORRECTION

| | | |
|---|---|---|
| PATENT NO. | : 12,372,647 B2 | Page 1 of 1 |
| APPLICATION NO. | : 18/561254 | |
| DATED | : July 29, 2025 | |
| INVENTOR(S) | : Hyungkyi Lee et al. | |

It is certified that error appears in the above-identified patent and that said Letters Patent is hereby corrected as shown below:

In the Specification

Column 7, Line 2, "on" should be --$\varphi n$--.

Column 13, Line 60, "2 cos($\Delta\varphi nm$)" should be --2cos($\Delta\varphi nm$)--.

Column 13, Lines 66-67, "2 cos($\Delta\varphi nm$)" should be --2cos($\Delta\varphi nm$)--.

Column 16, Line 5, a new paragraph should begin with --As shown--.

Signed and Sealed this
Thirtieth Day of September, 2025

John A. Squires
*Director of the United States Patent and Trademark Office*